United States Patent [19]

Elbe et al.

[11] Patent Number: 4,877,446
[45] Date of Patent: Oct. 31, 1989

[54] PESTICIDES BASED ON PYRIMIDINE DERIVATIVES

[75] Inventors: Hans-Ludwig Elbe, Wuppertal; Stefan Dutzmann, Duesseldorf; Paul Reinecke, Leverkusen, all of Fed. Rep. of Germany

[73] Assignee: Bayer Aktiengesellschaft, Leverkusen, Fed. Rep. of Germany

[21] Appl. No.: 146,996

[22] Filed: Jan. 22, 1988

[51] Int. Cl.$^4$ .................. A01N 43/54; C07D 239/26
[52] U.S. Cl. ........................ 71/92; 544/225; 544/335; 544/256
[58] Field of Search ............... 544/335, 225; 514/256; 71/92

[56] References Cited

U.S. PATENT DOCUMENTS

| | | | |
|---|---|---|---|
| 3,818,009 | 6/1974 | Taylor et al. | 544/335 |
| 4,436,907 | 3/1984 | Holmwood et al. | 544/335 |
| 4,525,204 | 6/1985 | Holmwood et al. | 544/335 |
| 4,584,373 | 4/1986 | Holmwood et al. | 544/335 |
| 4,713,456 | 12/1987 | Elbe et al. | 544/335 |

FOREIGN PATENT DOCUMENTS

| | | |
|---|---|---|
| 3048266 | 7/1982 | Fed. Rep. of Germany . |
| 3105374 | 9/1982 | Fed. Rep. of Germany . |
| 3210725 | 6/1983 | Fed. Rep. of Germany . |
| 3431689 | 3/1986 | Fed. Rep. of Germany . |

*Primary Examiner*—Cecilia Shen
*Attorney, Agent, or Firm*—Sprung Horn Kramer & Woods

[57] ABSTRACT

A method of combating fungi which comprises applying to such fungi or to a fungus habitat a fungicidally effective amount of a substituted pyrimidine of the formula

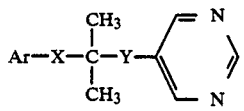

in which
Ar represents optionally substituted phenyl,
X represents oxygen, sulphur, sulphinyl, sulphonyl or one of the groups —$CH_2$—; —O—$CH_2$—; —$CHhd 2$—O—; O—$CH_2$—$CH_2$—; —$S(O)_n$—$CH_2$—; —$CH_2$—$S(O)_n$—or —$S(O)_n$—$CH_2$—$CH_2$—, and
Y represents on eof the groups

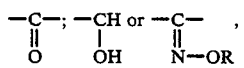

where
R represents hydrogen, alkyl, alkenyl, alkinyl or optionally substituted aralkyl, and
n represents a number 0, 1 or 2, or an acid-additonal salt or metal-salt complex thereof.
Most of the compounds are new.

12 Claims, No Drawings

PESTICIDES BASED ON PYRIMIDINE DERIVATIVES

The invention relates to the use of pyrimidine compounds, some of which are known, as pesticides, in particular as fungicides.

It has already been disclosed that certain pyrimidine derivatives, such as, for example, 5-[1-(4-chlorobenzyloxy)-2-methyl-prop-1-yl]-phyimidine or 5-[1-(4-trifluoromethoxybenzyloxy)-2,2-dimethyl-prop-1-yl]-pyrimidine, have fungicidal properties (cf. DE-OS (German Published Specification) 3,105,374 corresponding to U.S. Pat. No. 4436907).

However, the activity of these previously known compounds is not completely satisfactory in all areas of application, in particular at low application rates and concentrations.

Furthermore, certain substituted pyrimidines, such as, for example, 2,2-dimethyl-3-(4-fluorophenyl)-1-(5-pyrimidinyl)-propan-1-one or 2,2-dimethyl-3-(3-chlorophenoxy)-1-(5-pyrimidinyl-propan-1-one or 2,2-dimethyl-3-(4-chlorophenoxy)-1-(5-pyrimidinyl)-propan-1-one, have been disclosed (cf. German DE-OS 3,431,689 corresponding to U.S. Ser. No. 769,639 filed on Aug. 26, 1985, pending). However, nothing is known on the fungicidal activity of these previously known pyrimidines.

It has been found that substituted pyrimidines of the general formula (I)

$$Ar-X-\underset{\underset{CH_3}{|}}{\overset{\overset{CH_3}{|}}{C}}-Y-\underset{N}{\overset{N}{\diagup\!\!\!\!\diagdown}}\quad (I)$$

in which

Ar represents optionally substituted phenyl,

X represents oxygen, sulphur, sulphinyl, sulphonyl or one of the groups $-CH_2-$; $-O-CH_2-$; $-CH_2-O-$; $-O-CH_2-CH_2-$; $-S(O)_n-CH_2-$; $-CH_2-S(O)_n-$ or $-S(O)_n-CH_2-CH_2-$, and Y represents one of the groups $$-\underset{\underset{O}{||}}{C}-;\quad -\underset{\underset{OH}{|}}{CH}\text{ or }-\underset{\underset{N-OR}{||}}{C}-\;,$$

where

R represents hydrogen, alkyl, alkenyl, alkinyl or optionally substituted aralkyl, and n represents a number 0, 1 or 2, some of which are known, and the acid-addition salts and metal-salt complexes thereof, have a good action against pests.

The compounds of the formula (I) may, if appropriate, exist as geometrical and/or optical isomers or isomeric mixtures of various composition. The pure isomers and the isomeric mixtures are claimed according to the invention.

Surpisingly, the substituted pyrimidines of the general formula (I) which can be used according to the invention have, inter alia, a considerably better fungicidal activity than the substituted pyrimidine derivatives known from the prior art as fungicides, such as, for example, 5-[1-(4-chlorobenzyloxy)-2-methyl-prop-1-yl]-pyrimidine or 5-[1-(4-trifluoromethoxybenzyloxy)-2,2-dimethylprop-1-yl]-pyrimidine, which are similar compounds chemically and regarding their action.

Formula (I) provides a general definition of the substituted pyrimidines which can be used according to the invention. Compounds of the formula (I) which can preferably be used are those which Ar represents phenyl which is optionally monosubstituted to polysubstituted by identical or different substituents, suitable substituents being: halogen, cyano, nitro and in each case straight-chain or branched alkyl, alkoxy, alkylthio, alkylsulphinyl or alkylsulphonyl in each case having 1 to 4 carbon atoms, in each case straight-chain or branched halogenoalkyl, halogenoalkoxy, halogenoalkythio, halogenoalkylsulphinyl or halogenoalkylsulphonyl in each case having 1 to 4 carbon atoms and 1 to 9 identical or different halogen atoms, in each case straight-chain or branched alkoxycarbonyl or alkoximinoalkyl in each case having 1 to 4 carbon atoms in the individual alkyl parts, doubly linked dioxyalkylene which is optionally monosubstituted to polysubstituted by identical or different halogen, or pheny or phenoxy which is in each case optionally monosubstituted to polysubstituted by identical or different halogen, X represents oxygen, sulphur, sulphinyl, sulphonyl or one of the groups $-CH_2-$; $-O-CH_2-$; $-CH_2-O-$; $-O-CH_2-CH_2-$; $-S(O)_n-CH_2-$: $-CH_2-S(O)_n-$ or $-S(O)_n-CH_2-CH_2-$, and Y represents one of the groups $$-\underset{\underset{O}{||}}{C}-;\quad -\underset{\underset{OH}{|}}{CH}\text{ or }-\underset{\underset{N-OR}{||}}{C}-\;,$$

where

R represents hydrogen or in each case straight-chain or branched alkyl having 1 to 6 carbon atoms, alkenyl having 3 to 5 carbon atoms or alkinyl having 3 to 5 carbon atoms, or benzyl or phenylethyl which is in each case optionally monosubstituted to polysubstituted by identical or different substitutents, suitable substituents in the phenyl part in each case being those mentioned in the case of the Ar radical, and n represents a number 0, 1 or 2.

Compounds of the formula (I) which can particularly preferably be used according to the invention are those in which Ar represents phenyl which is optionally monosubstituted, disubstituted or trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, ethylthio, trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethoxy, difluoromethoxy, fluoromethoxy, dichlorofluoromethoxy, difluorochloromethoxy, difluorobromomethoxy, trichloromethoxy, trifluoroethoxy, tetrafluoroethoxy, pentafluoroethoxy, trifluorochloroethoxy, trifluorodichloroethoxy, difluorotrichloroethoxy, pentachloroethoxy, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethysulphonyl, dichlorofluoromethylsulphonyl, difluorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, difluorodioxymethylene, tetrafluorodioxyethylene, trifluorodioxyethylene, difluorodioxyethylene, dioxymethylene or dioxyethylene, or phenyl or phenoxy which is in each case optionally monosubstituted, disubstituted or trisubstituted by fluorine or chlorine, X represents oxygen, sulphur, sulphinyl, sulphonyl or one of the groups —CH$_2$—; —O—CH$_2$—; —CH$_2$—O—; —O—CH$_2$—CH$_2$—; —S(O)$_n$—CH$_2$—; —CH$_2$—S(O)$_n$— or —S(O)$_n$—CH$_2$—CH$_2$—, and Y represents one of the groups $$-\underset{\underset{O}{\|}}{C}-;\quad -\underset{\underset{OH}{|}}{CH}-\quad\text{or}\quad -\underset{\underset{N-OR}{\|}}{C}-$$

where

R represents hydrogen, methyl, ethyl, n- or i-propyl, allyl or propargyl, or benzyl which is optionally monosubstituted, disubstituted or trisubstituted by identical or different substituents, suitable substituents being those mentioned in the case of the Ar radical, and n represents a number 0, 1 or 2.

Preferred compounds which can be used according to the invention are also products of the addition reaction of acids with those substituted pyrimidines of the formula (I) in which the substituents Ar, X and Y have the meaning which has already been mentioned as preferred for these substituents.

The acids which can take part in the addition reaction preferably include hydrohalic acids, such as, for example, hydrochloric acid and hydrobromic acid, in particular hydrochloric acid, furthermore phosphoric acid, nitric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as p-toluenesulphonic acid and 1,5-naphthalenedisulphonic acid.

Compounds which can additionally be preferably used according to the invention are products of the addition reaction of salts of metals of main group II to IV and subgroup I and II and IV to VIII with those substituted pyrimidines of the formula (I) in which the substituents Ar, X and Y have the meanings which have already been mentioned as being preferred for these substituents.

Salts of copper, zinc, manganese, magnesium, tin, iron and nickel are particularly preferred here. Possible anions of these salts are those which are derived from acids which lead to physiologically acceptable addition products. In this connection, particularly preferred such acids are hydrohalic acids, such as, for example, hydrochloric acid and hydrobromic acid, furthermore phosphoric acid, nitric acid and sulphuric acid.

In addition to the compound mentioned in the preparation examples, the following substituted pyrimidines of the general formula (I) may be mentioned individually:

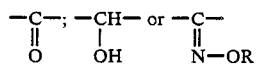
(I)

| Ar | X | Y | X | Y |
|---|---|---|---|---|
| F—⌬— | O | —C(=O)— | O | —CH(OH)— |
| 2,4-F$_2$-C$_6$H$_3$— | O | —C(=O)— | O | —CH(OH)— |
| F$_3$C—⌬— | O | —C(=O)— | O | —CH(OH)— |
| F$_3$CO—⌬— | O | —C(=O)— | O | =CH(OH)— |
| F$_3$CS—⌬— | O | —C(=O)— | O | —CH(OH)— |

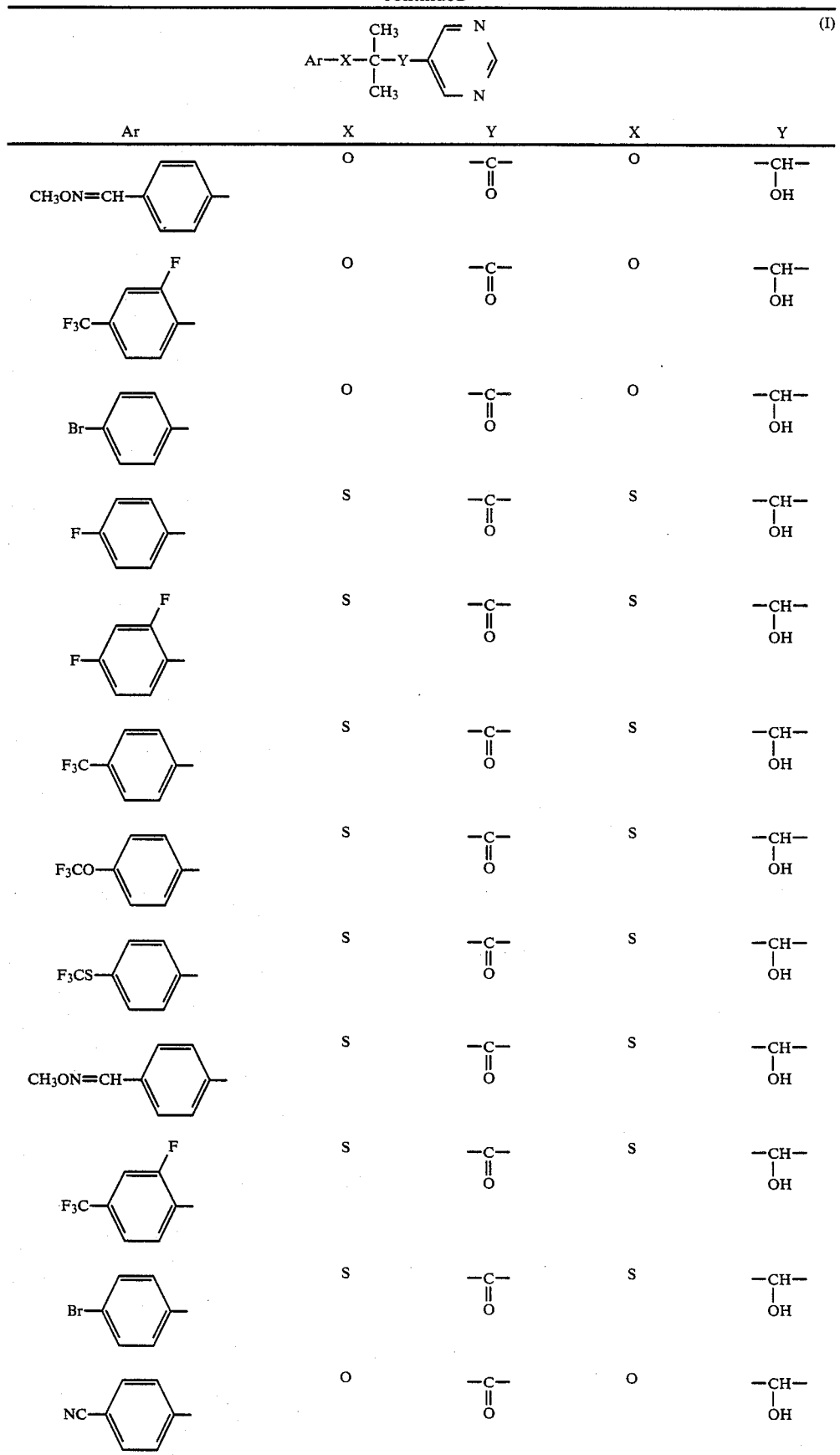

-continued
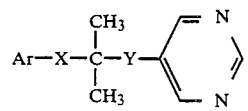
(I)
| Ar | X | Y | X | Y |
|---|---|---|---|---|
| 4-CH₃-C₆H₄- | O | -C(=O)- | O | -CH(OH)- |
| 3-CH₃-C₆H₄- | O | -C(=O)- | O | -CH(OH)- |
| 2-CH₃-C₆H₄- | O | -C(=O)- | O | -CH(OH)- |
| 4-FCl₂CO-C₆H₄- | O | -C(=O)- | O | -CH(OH)- |
| 4-FClCHO-C₆H₄- | O | -C(=O)- | O | -CH(OH)- |
| 4-F₂ClCO-C₆H₄- | O | -C(=O)- | O | -CH(OH)- |
| 4-F₂CHO-C₆H₄- | O | -C(=O)- | O | -CH(OH)- |
| 4-FCl₂CS-C₆H₄- | O | -C(=O)- | O | -CH(OH)- |
| 4-F₂ClCS-C₆H₄- | O | -C(=O)- | O | -CH(OH)- |
| 4-F₂CHS-C₆H₄- | O | -C(=O)- | O | -CH(OH)- |
| 4-Br-C₆H₄- | -CH₂-O- | -C(=O)- | -CH₂-O- | -CH(OH)- |
| 4-Cl-C₆H₄- | -CH₂-O- | -C(=O)- | -CH₂-O- | -CH(OH)- |

-continued $$Ar-X-\underset{CH_3}{\overset{CH_3}{\underset{|}{C}}}-Y-\underset{N}{\overset{N}{\diagdown}}\diagup$$ (I)

| Ar | X | Y | X | Y |
|---|---|---|---|---|
| 4-NC-C6H4- | S | -C(=O)- | S | -CH(OH)- |
| 4-CH3-C6H4- | S | -C(=O)- | S | -CH(OH)- |
| 3-CH3-C6H4- | S | -C(=O)- | S | -CH(OH)- |
| 2-CH3-C6H4- | S | -C(=O)- | S | -CH(OH)- |
| 4-FCl2CO-C6H4- | S | -C(=O)- | S | -CH(OH)- |
| 4-FClCHO-C6H4- | S | -C(=O)- | S | -CH(OH)- |
| 4-F2ClCO-C6H4- | S | -C(=O)- | S | -CH(OH)- |
| 4-F2CHO-C6H4- | S | -C(=O)- | S | -CH(OH)- |
| 4-FCl2CS-C6H4- | S | -C(=O)- | S | -CH(OH)- |
| 4-F2ClCS-C6H4- | S | -C(=O)- | S | -CH(OH)- |
| 4-F2CHS-C6H4- | S | -C(=O)- | S | -CH(OH)- |
| 4-Br-C6H4- | -CH2-O- | -C(=N-OH)- | -CH2-O- | -C(=N-OCH3)- |

-continued $$\text{Ar}-\text{X}-\underset{\underset{CH_3}{|}}{\overset{\overset{CH_3}{|}}{C}}-\text{Y}-\underset{\underset{N}{\diagdown\diagup}}{\overset{\overset{N}{\diagup\diagdown}}{\phantom{X}}} \quad (I)$$

| Ar | X | Y | X | Y |
|---|---|---|---|---|
| 4-Cl-C6H4- | -CH2-O- | -C(=N-OH)- | -CH2-O- | -C(=N-OCH3)- |
| 2,4-Cl2-C6H3- | -CH2-O- | -C(=O)- | -CH2-O- | -CH(OH)- |
| 3,4-Cl2-C6H3- | -CH2-O- | -C(=O)- | -CH2-O- | -CH(OH)- |
| 4-F3CO-C6H4- | -CH2-O- | -C(=O)- | -CH2-O- | =CH(OH)- |
| 4-F3CS-C6H4- | -CH2-O- | -C(=O)- | -CH2-O- | -CH(OH)- |
| 4-F-C6H4- | -CH2-O- | -C(=O)- | -CH2-O- | -CH(OH)- |
| 3-F3C-4-F-C6H3- | -CH2-O- | -C(=O)- | -CH2-O- | -CH(OH)- |
| 2-F-4-F-C6H3- | -CH2-O- | -C(=O)- | -CH2-O- | -CH(OH)- |
| 3-F-4-F3C-C6H3- | -CH2- | -C(=O)- | -CH2- | -CH(OH)- |
| 3-Br-4-F3C-C6H3- | -CH2- | -C(=O)- | -CH2- | -CH(OH)- |
| 2,4-F2-C6H3- | -CH2- | -C(=O)- | -CH2- | -CH(OH)- |

-continued

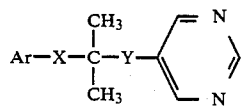
(I)

| Ar | X | Y | X | Y |
|---|---|---|---|---|
| 3-F, 4-CF$_3$-phenyl | —CH$_2$— | —C(=O)— | —CH$_2$— | =CH—OH |
| 3,5-F$_2$, 4-CF$_3$-phenyl | —CH$_2$— | —C(=O)— | —CH$_2$— | —CH(OH)— |
| 2,4-Cl$_2$-phenyl | —CH$_2$—O— | —C(=N—OH)— | —CH$_2$—O— | —C(=N—OCH$_3$)— |
| 3,4-Cl$_2$-phenyl | —CH$_2$—O— | —C(=N—OH)— | —CH$_2$—O— | —C(=N—OCH$_3$)— |
| 4-F$_3$CO-phenyl | —CH$_2$—O— | —C(=N—OH)— | —CH$_2$—O— | —C(=N—OCH$_3$)— |
| 4-F$_3$CS-phenyl | —CH$_2$—O— | —C(=N—OH)— | —CH$_2$—O— | —C(=N—OCH$_3$)— |
| 4-F-phenyl | —CH$_2$—O— | —C(=N—OH)— | —CH$_2$—O— | —C(=N—OCH$_3$)— |
| 2-CF$_3$, 4-F-phenyl | —CH$_2$—O— | —C(=N—OH)— | —CH$_2$—O— | —C(=N—OCH$_3$)— |
| 2,4-F$_2$-phenyl | —CH$_2$—O— | —C(=N—OH)— | —CH$_2$—O— | —C(=N—OCH$_3$)— |
| 3-F, 4-CF$_3$-phenyl | —CH$_2$— | —C(=N—OH)— | —CH$_2$— | —C(=N—OCH$_3$)— |

-continued $$Ar-X-\underset{CH_3}{\overset{CH_3}{\overset{|}{C}}}-Y-\underset{N}{\overset{N}{\diagdown}}\diagup \tag{I}$$

| Ar | X | Y | X | Y |
|---|---|---|---|---|
| 2-Br-4-(substituent), 1-CF₃ phenyl | —CH₂— | —C(=N-OH)— | —CH₂— | —C(=N-OCH₃)— |
| 2,4-F₂ phenyl | —CH₂— | —C(=N-OH)— | —CH₂— | —C(=N-OCH₃)— |
| 3-F-4-(substituent), 1-CF₃ phenyl | —CH₂— | —C(=N-OH)— | —CH₂— | —C(=N-OCH₃)— |
| 2,6-F₂-4-CF₃ phenyl | —CH₂— | —C(=N-OH)— | —CH₂— | —C(=N-OCH₃)— |
| 2,5-Cl₂-4-CF₃ phenyl | —CH₂— | —C(=O)— | —CH₂— | —CH(OH)— |
| 2-Cl-4-CF₃ phenyl | —CH₂— | —C(=O)— | —CH₂— | =CH(OH)— |
| 4-CF₃ phenyl | —CH₂— | —C(=O)— | —CH₂— | —CH(OH)— |
| 4-OCHF₂ phenyl | —CH₂— | —C(=O)— | —CH₂— | —CH(OH)— |
| 2-Cl-4-OCHF₂ phenyl | —CH₂— | —C(=O)— | —CH₂— | —CH(OH)— |
| 2-OCHF₂-5-Cl phenyl | —CH₂— | —C(=O)— | —CH₂— | —CH(OH)— |

-continued $$Ar-X-\underset{\underset{CH_3}{|}}{\overset{\overset{CH_3}{|}}{C}}-Y-\underset{N}{\overset{N}{\diagup}}\!\!\!\diagdown \quad (I)$$

| Ar | X | Y | X | Y |
|---|---|---|---|---|
| 2-F, 3-OCHF₂-phenyl | —CH₂— | —C(=O)— | —CH₂— | —CH(OH)— |
| 2-OCF₃, 3-Cl-phenyl | —CH₂— | —C(=O)— | —CH₂— | —CH(OH)— |
| 2-OCF₃, 3,5-diCl-phenyl | —CH₂— | —C(=O)— | —CH₂— | —CH(OH)— |
| 2-OCF₂Cl, 3-Cl-phenyl | —CH₂— | —C(=O)— | —CH₂— | —CH(OH)— |
| 2-OCF₂Cl, 3,5-diCl-phenyl | —CH₂— | —C(=O)— | —CH₂— | —CH(OH)— |
| 2-OCF₃, 3-Br-phenyl | —CH₂— | —C(=O)— | —CH₂— | —CH(OH)— |
| 2,4-diCl, 5-CF₃-phenyl | —CH₂— | —C(=N—OH)— | —CH₂— | —C(=N—OCH₃)— |
| 2-CF₃, 3-Cl-phenyl | —CH₂— | —C(=N—OH)— | —CH₂— | —C(=N—OCH₃)— |
| 4-CF₃-phenyl | —CH₂— | —C(=N—OH)— | —CH₂— | —C(=N—OCH₃)— |
| 4-OCHF₂-phenyl | —CH₂— | —C(=N—OH)— | —CH₂— | —C(=N—OCH₃)— |

-continued
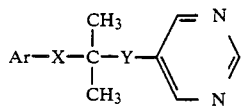
| Ar | X | Y | X | Y |
|---|---|---|---|---|
| 2-Cl, 4-(F₂CHO) phenyl | —CH₂— | —C(=N-OH)— | —CH₂— | —C(=N-OCH₃)— |
| 3-(F₂CHO), 4-Cl phenyl | —CH₂— | —C(=N-OH)— | —CH₂— | —C(=N-OCH₃)— |
| 3-(F₂CHO), 4-F phenyl | —CH₂— | —C(=N-OH)— | —CH₂— | —C(=N-OCH₃)— |
| 2-Cl, 4-(F₃CO) phenyl | —CH₂— | —C(=N-OH)— | —CH₂— | —C(=N-OCH₃)— |
| 2,4-Cl₂, 3-(F₃CO) phenyl | —CH₂— | —C(=N-OH)— | —CH₂— | —C(=N-OCH₃)— |
| 2-Cl, 4-(ClF₂CO) phenyl | —CH₂— | —C(=N-OH)— | —CH₂— | —C(=N-OCH₃)— |
| 2,4-Cl₂, 3-(ClF₂CO) phenyl | —CH₂— | —C(=N-OH)— | —CH₂— | —C(=N-OCH₃)— |
| 2-Br, 4-(F₃CO) phenyl | —CH₂— | —C(=N-OH)— | —CH₂— | —C(=N-OCH₃)— |
| 2,4-Br₂, 3-(ClF₂CO) phenyl | —CH₂— | —C(=O)— | —CH₂— | —CH(OH)— |

-continued $$Ar-X-\underset{CH_3}{\overset{CH_3}{\underset{|}{C}}}-Y-\text{pyrimidine}$$ (I)

| Ar | X | Y | X | Y |
|---|---|---|---|---|
| 3-Cl, 2-F₃CO-phenyl | —CH₂— | —C(=O)— | —CH₂— | —CH(OH)— |
| 3-F, 2-F₃CO-phenyl | —CH₂— | —C(=O)— | —CH₂— | —CH(OH)— |
| 3-Cl, 4-F₃CO-phenyl | —CH₂— | —C(=O)— | —CH₂— | —CH(OH)— |
| 3-ClF₂CO-phenyl | —CH₂— | —C(=O)— | —CH₂— | —CH(OH)— |
| 4-ClF₂CO-phenyl | —CH₂— | —C(=O)— | —CH₂— | —CH(OH)— |
| 2-F, 4-F₃CO-phenyl | —CH₂— | —C(=O)— | —CH₂— | —CH(OH)— |
| 3-F, 4-F₃CO-phenyl | —CH₂— | —C(=O)— | —CH₂— | —CH(OH)— |
| 2-Cl, 4-F₃CO-phenyl | —CH₂— | —C(=O)— | —CH₂— | —CH(OH)— |
| 2-ClF₂CO, 5-Cl-phenyl | —CH₂— | —C(=O)— | —CH₂— | —CH(OH)— |

-continued $$Ar-X-\underset{CH_3}{\overset{CH_3}{C}}-Y-\text{(pyrimidine)} \qquad (I)$$

| Ar | X | Y | X | Y |
|---|---|---|---|---|
| 4-Cl, 3-(ClF₂CO) phenyl | —CH₂— | —C(=O)— | —CH₂— | —CH(OH)— |
| 4-(F₂CH—CF₂—O) phenyl | —CH₂— | —C(=O)— | —CH₂— | —CH(OH)— |
| 3,5-Br₂, 4-(ClF₂CO) phenyl | —CH₂— | —C(=N—OH)— | —CH₂— | —C(=N—OCH₃)— |
| 4-Cl, 3-(F₃CO) phenyl | —CH₂— | —C(=N—OH)— | —CH₂— | —C(=N—OCH₃)— |
| 4-F, 3-(F₃CO) phenyl | —CH₂— | —C(=N—OH)— | —CH₂— | —C(=N—OCH₃)— |
| 4-Cl, 3-(F₃CO) phenyl | —CH₂— | —C(=N—OH)— | —CH₂— | —C(=N—OCH₃)— |
| 3-(ClF₂CO) phenyl | —CH₂— | —C(=N—OH)— | —CH₂— | —C(=N—OCH₃)— |
| 4-(ClF₂CO) phenyl | —CH₂— | —C(=N—OH)— | —CH₂— | —C(=N—OCH₃)— |
| 3-F, 4-(F₃CO) phenyl | —CH₂— | —C(=N—OH)— | —CH₂— | —C(=N—OCH₃)— |

-continued $$Ar-X-\underset{\underset{CH_3}{|}}{\overset{\overset{CH_3}{|}}{C}}-Y-\underset{\text{(pyrimidine)}}{} \quad (I)$$

| Ar | X | Y | X | Y |
|---|---|---|---|---|
| 3-F, 4-F₃CO-phenyl | —CH₂— | —C(=N—OH)— | —CH₂— | —C(=N—OCH₃)— |
| 3-Cl, 4-F₃CO-phenyl | —CH₂— | —C(=N—OH)— | —CH₂— | —C(=N—OCH₃)— |
| 2-ClF₂CO, 5-Cl-phenyl | —CH₂— | —C(=N—OH)— | —CH₂— | —C(=N—OCH₃)— |
| 3-Cl, 4-ClF₂CO-phenyl | —CH₂— | —C(=N—OH)— | —CH₂— | —C(=N—OCH₃)— |
| 4-(F₂CH—CF₂—O)-phenyl | —CH₂— | —C(=N—OH)— | —CH₂— | —C(=N—OCH₃)— |
| 3-Cl, 4-(F₂CH—CF₂—O)-phenyl | —CH₂— | —C(=O)— | —CH₂— | —CH(OH)— |
| 3-(F₂CH—CF₂—O), 4-Cl-phenyl | —CH₂— | —C(=O)— | —CH₂— | —CH(OH)— |
| 4-(FClCH—CF₂—O)-phenyl | —CH₂— | —C(=O)— | —CH₂— | —CH(OH)— |
| 3-Cl, 4-(FClCH—CF₂—O)-phenyl | —CH₂— | —C(=O)— | —CH₂— | —CH(OH)— |
| 4-(F₂CHS)-phenyl | —CH₂— | —C(=O)— | —CH₂— | —CH(OH)— |

-continued $$Ar-X-\underset{\underset{CH_3}{|}}{\overset{\overset{CH_3}{|}}{C}}-Y-\underset{N}{\overset{N}{\diagdown}}\diagup \quad (I)$$

| Ar | X | Y | X | Y |
|---|---|---|---|---|
| 2-Cl, 4-(F₂CHS)-phenyl | —CH₂— | —C(=O)— | —CH₂— | —CH(OH)— |
| 2-CH₃, 4-(F₂CHS)-phenyl | —CH₂— | —C(=O)— | —CH₂— | —CH(OH)— |
| 2-Cl, 4-(F₃CS)-phenyl | —CH₂— | —C(=O)— | —CH₂— | —CH(OH)— |
| 2,6-Cl₂, 4-(F₃CS)-phenyl | —CH₂— | —C(=O)— | —CH₂— | —CH(OH)— |
| 3-Cl, 4-(ClF₂CS)-phenyl | —CH₂— | —C(=O)— | —CH₂— | —CH(OH)— |
| 3,5-Cl₂, 4-(ClF₂CS)-phenyl | —CH₂— | —C(=O)— | —CH₂— | —CH(OH)— |
| 3-Br, 4-(F₃CS)-phenyl | —CH₂— | —C(=O)— | —CH₂— | —CH(OH)— |
| 2-Cl, 4-(F₂CH—CF₂—O)-phenyl | —CH₂— | —C(=N—OH)— | —CH₂— | —C(=N—OCH₃)— |
| 2-Cl, 5-(F₂CH—CF₂—O)-phenyl | —CH₂— | —C(=N—OH)— | —CH₂— | —C(=N—OCH₃)— |

-continued $$\text{Ar}-\text{X}-\underset{\underset{\text{CH}_3}{|}}{\overset{\overset{\text{CH}_3}{|}}{\text{C}}}-\text{Y}-\underset{}{\overset{}{\underset{N}{\overset{N}{\diagup\diagdown}}}}$$ (I)

| Ar | X | Y | X | Y |
|---|---|---|---|---|
| 4-(FClCH—CF₂O)—C₆H₄— | —CH₂— | —C(=N—OH)— | —CH₂— | —C(=N—OCH₃)— |
| 3-Cl-4-(FClCH—CF₂O)—C₆H₃— | —CH₂— | —C(=N—OH)— | —CH₂— | —C(=N—OCH₃)— |
| 4-(F₂CHS)—C₆H₄— | —CH₂— | —C(=N—OH)— | —CH₂— | —C(=N—OCH₃)— |
| 3-Cl-4-(F₂CHS)—C₆H₃— | —CH₂— | —C(=N—OH)— | —CH₂— | —C(=N—OCH₃)— |
| 3-CH₃-4-(F₂CHS)—C₆H₃— | —CH₂— | —C(=N—OH)— | —CH₂— | —C(=N—OCH₃)— |
| 3-Cl-4-(F₃CS)—C₆H₃— | —CH₂— | —C(=N—OH)— | —CH₂— | —C(=N—OCH₃)— |
| 3,5-Cl₂-4-(F₃CS)—C₆H₂— | —CH₂— | —C(=N—OH)— | —CH₂— | —C(=N—OCH₃)— |
| 3-Cl-4-(ClF₂CS)—C₆H₃— | —CH₂— | —C(=N—OH)— | —CH₂— | —C(=N—OCH₃)— |
| 3,5-Cl₂-4-(ClF₂CS)—C₆H₂— | —CH₂— | —C(=N—OH)— | —CH₂— | —C(=N—OCH₃)— |
| 3-Br-4-(F₃CS)—C₆H₃— | —CH₂— | —C(=N—OH)— | —CH₂— | —C(=N—OCH₃)— |

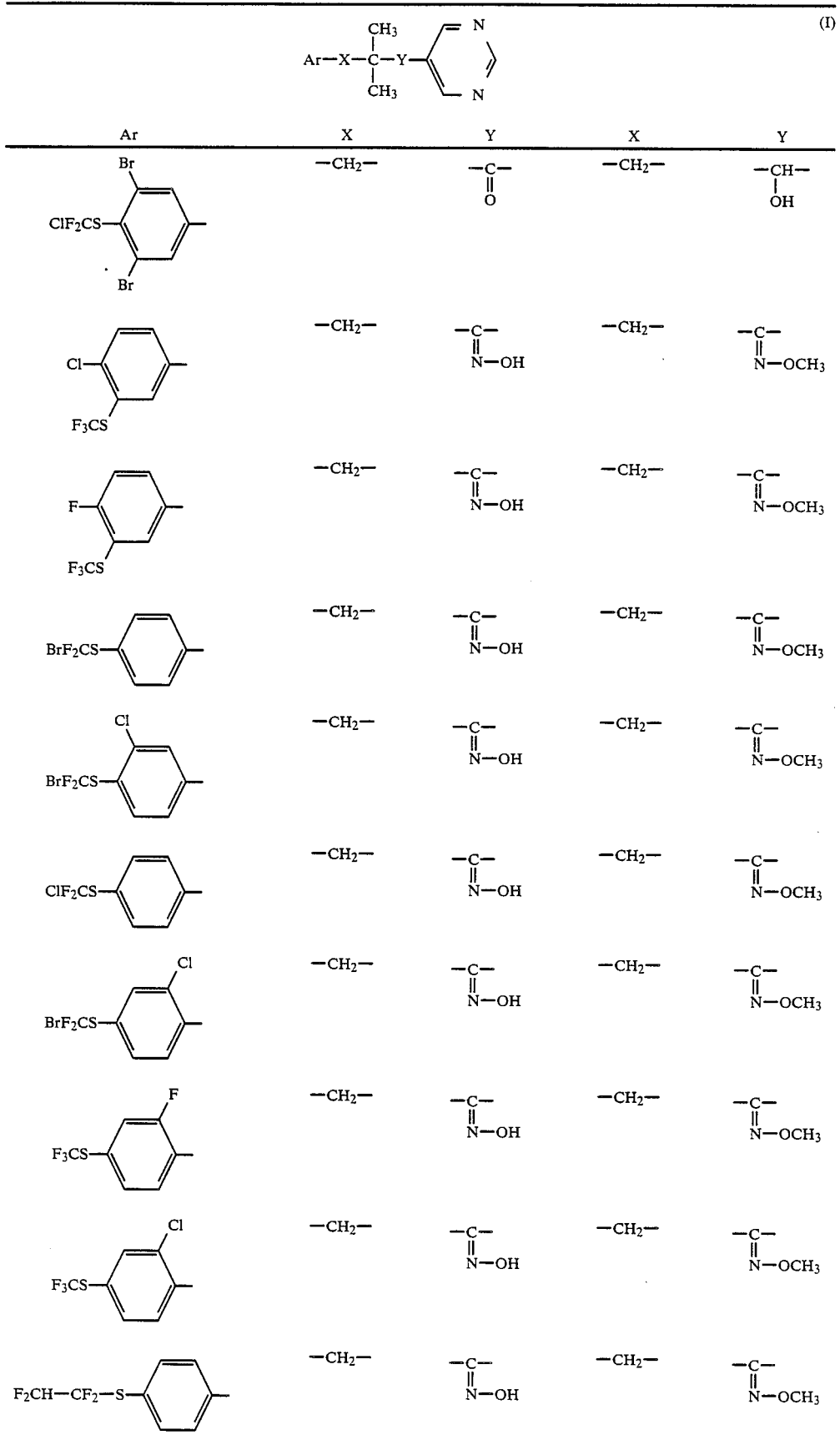

-continued $$Ar-X-\underset{\underset{CH_3}{|}}{\overset{\overset{CH_3}{|}}{C}}-Y-\begin{pmatrix}\text{pyrimidine}\end{pmatrix} \quad (I)$$

| Ar | X | Y | X | Y |
|---|---|---|---|---|
| 2-Cl, 4-(F₂CH—CF₂—S) phenyl | —CH₂— | —C(=N—OH)— | —CH₂— | —C(=N—OCH₃)— |
| 2-Br, 6-Br, 4-(ClF₂CS) phenyl | —CH₂— | —C(=N—OH)— | —CH₂— | —C(=N—OCH₃)— |
| 2-Cl, 3-(F₃CS) phenyl | —CH₂— | —C(=N—OH)— | —CH₂— | —C(=N—OCH₃)— |
| 2-F, 3-(F₃CS) phenyl | —CH₂— | —C(=N—OH)— | —CH₂— | —C(=N—OCH₃)— |
| 4-(BrF₂CS) phenyl | —CH₂— | —C(=N—OH)— | —CH₂— | —C(=N—OCH₃)— |
| 2-Cl, 4-(BrF₂CS) phenyl | —CH₂— | —C(=N—OH)— | —CH₂— | —C(=N—OCH₃)— |
| 4-(ClF₂CS) phenyl | —CH₂— | —C(=N—OH)— | —CH₂— | —C(=N—OCH₃)— |
| 3-Cl, 4-(BrF₂CS) phenyl | —CH₂— | —C(=N—OH)— | —CH₂— | —C(=N—OCH₃)— |
| 2-F, 4-(F₃CS) phenyl | —CH₂— | —C(=N—OH)— | —CH₂— | —C(=N—OCH₃)— |
| 2-Cl, 4-(F₃CS) phenyl | —CH₂— | —C(=N—OH)— | —CH₂— | —C(=N—OCH₃)— |

-continued $$Ar-X-\underset{\underset{CH_3}{|}}{\overset{\overset{CH_3}{|}}{C}}-Y-\text{(pyrimidine)} \tag{I}$$

| Ar | X | Y | X | Y |
|---|---|---|---|---|
| 4-(F₂CH-CF₂-S)-C₆H₄- | -CH₂- | -C(=N-OH)- | -CH₂- | -C(=N-OCH₃)- |
| 3-Cl-4-(F₂CH-CF₂-S)-C₆H₃- | -CH₂- | -C(=N-OH)- | -CH₂- | -C(=N-OCH₃)- |
| 2-(CHF₂-O)-C₆H₄-O- (benzodioxole-type, CF₂ bridge) | -CH₂- | -C(=O)- | -CH₂- | -CH(OH)- |
| 2,3-dihydro-2-F-(CF₂-O)(O)-C₆H₃- | -CH₂- | -C(=O)- | -CH₂- | -CH(OH)- |
| 2,2,3-trifluoro-benzodioxole derivative (CF₂-CF-O) | -CH₂- | -C(=O)- | -CH₂- | -CH(OH)- |
| 4-(F₃CO)-C₆H₄- | -O-CH₂- | -C(=O)- | -O-CH₂- | -CH(OH)- |
| 4-(F₃CS)-C₆H₄- | -O-CH₂- | -C(=O)- | -O-CH₂- | -CH(OH)- |
| 4-F-C₆H₄- | -O-CH₂- | -C(=O)- | -O-CH₂- | -CH(OH)- |
| 2,4-F₂-C₆H₃- | -O-CH₂- | -C(=O)- | -O-CH₂- | -CH(OH)- |
| 4-Br-C₆H₄- | -O-CH₂- | -C(=O)- | -O-CH₂- | -CH(OH)- |
| 4-CH₃-C₆H₄- | -O-CH₂- | -C(=O)- | -O-CH₂- | -CH(OH)- |

-continued $$Ar-X-\underset{\underset{CH_3}{|}}{\overset{\overset{CH_3}{|}}{C}}-Y-\underset{\underset{N}{\parallel}}{\overset{\overset{N}{\parallel}}{\diagup}}$$ (I)

| Ar | X | Y | X | Y |
|---|---|---|---|---|
| 4-CH₃O-C₆H₄- | -O-CH₂- | -C(=O)- | -O-CH₂- | -CH(OH)- |
| 3-CH₃O-C₆H₄- | -O-CH₂- | -C(=O)- | -O-CH₂- | -CH(OH)- |
| 2-CH₃O-C₆H₄- | -O-CH₂- | -C(=O)- | -O-CH₂- | -CH(OH)- |
| 3,4-(OCF₂O)-C₆H₃- | -CH₂- | -C(=N-OH)- | -CH₂- | -C(=N-OCH₃)- |
| 3,4-(OCHFCF₂O)-C₆H₃- | -CH₂- | -C(=N-OH)- | -CH₂- | -C(=N-OCH₃)- |
| 3,4-(OCF₂CF₂O)-C₆H₃- | -CH₂- | -C(=N-OH)- | -CH₂- | -C(=N-OCH₃)- |
| 4-F₃CO-C₆H₄- | -S-CH₂- | -C(=O)- | -S-CH₂- | -CH(OH)- |
| 4-F₃CS-C₆H₄- | -S-CH₂- | -C(=O)- | -S-CH₂- | -CH(OH)- |
| 4-F-C₆H₄- | -S-CH₂- | -C(=O)- | -S-CH₂- | -CH(OH)- |
| 2,4-F₂-C₆H₃- | -S-CH₂- | -C(=O)- | -S-CH₂- | -CH(OH)- |
| 4-Br-C₆H₄- | -S-CH₂- | -C(=O)- | -S-CH₂- | -CH(OH)- |

-continued $$Ar-X-\underset{\underset{CH_3}{|}}{\overset{\overset{CH_3}{|}}{C}}-Y-\underset{N}{\overset{N}{\diagup}}\diagdown \quad (I)$$

| Ar | X | Y | X | Y |
|---|---|---|---|---|
| 4-CH₃-C₆H₄- | —S—CH₂— | —C(=O)— | —S—CH₂— | —CH(OH)— |
| 4-CH₃O-C₆H₄- | —S—CH₂— | —C(=O)— | —S—CH₂— | —CH(OH)— |
| 3-CH₃O-C₆H₄- | —S—CH₂— | —C(=O)— | —S—CH₂— | —CH(OH)— |
| 2-CH₃O-C₆H₄- | —S—CH₂— | —C(=O)— | —S—CH₂— | —CH(OH)— |
| 2-F-4-F₃C-C₆H₃- | —O—CH₂— | —C(=O)— | —S—CH₂— | —C(=O)— |
| 4-F₃C-C₆H₄- | —O—CH₂— | —C(=O)— | —S—CH₂— | —C(=O)— |
| 4-NC-C₆H₄- | —O—CH₂— | —C(=O)— | —S—CH₂— | —C(=O)— |
| 4-(CH₃ON=CH)-C₆H₄- | —O—CH₂— | —C(=O)— | —S—CH₂— | —C(=O)— |
| 3,5-Cl₂-C₆H₃- | —O—CH₂— | —C(=O)— | —S—CH₂— | —C(=O)— |
| 3,4-Cl₂-C₆H₃- | —O—CH₂— | —C(=O)— | —S—CH₂— | —C(=O)— |
| 4-(ClF₂CS)-C₆H₄- | —O—CH₂— | —C(=O)— | —S—CH₂— | —C(=O)— |

-continued $$Ar-X-\underset{\underset{CH_3}{|}}{\overset{\overset{CH_3}{|}}{C}}-Y-\underset{\underset{N}{\diagdown}}{\overset{\diagup N}{\diagup}}\hspace{-2pt}\diagdown$$ (I)

| Ar | X | Y | X | Y |
|---|---|---|---|---|
| (CH₃)₃C—⟨C₆H₄⟩— (4-) | —O—CH₂— | —C(=O)— | —S—CH₂— | —C(=O)— |
| CH₃—⟨C₆H₄⟩— (4-) | —O—CH₂— | —C(=O)— | —S—CH₂— | —C(=O)— |
| 3-CH₃—⟨C₆H₄⟩— | —O—CH₂— | —C(=O)— | —S—CH₂— | —C(=O)— |
| 2-CH₃—⟨C₆H₄⟩— | —O—CH₂— | —C(=O)— | —S—CH₂— | —C(=O)— |
| FCl₂CO—⟨C₆H₄⟩— (4-) | —O—CH₂— | —C(=O)— | —S—CH₂— | —C(=O)— |
| 4-F₃C, 2-F—⟨C₆H₃⟩— | —O—CH₂— | —CH(OH)— | —S—CH₂— | —CH(OH)— |
| F₃C—⟨C₆H₄⟩— (4-) | —O—CH₂— | —CH(OH)— | —S—CH₂— | —CH(OH)— |
| NC—⟨C₆H₄⟩— (4-) | —O—CH₂— | —CH(OH)— | —S—CH₂— | —CH(OH)— |
| CH₃ON=CH—⟨C₆H₄⟩— | —O—CH₂— | —CH(OH)— | —S—CH₂— | —CH(OH)— |
| 3,5-Cl₂—⟨C₆H₃⟩— | —O—CH₂— | —CH(OH)— | —S—CH₂— | —CH(OH)— |
| 3,4-Cl₂—⟨C₆H₃⟩— | —O—CH₂— | —CH(OH)— | —S—CH₂— | —CH(OH)— |

-continued $$Ar-X-\underset{\underset{CH_3}{|}}{\overset{\overset{CH_3}{|}}{C}}-Y-\underset{}{\overset{}{\underset{N}{\overset{N}{\diagup\!\!\!\diagdown}}}} \quad (I)$$

| Ar | X | Y | X | Y |
|---|---|---|---|---|
| ClF₂CS—⟨C₆H₄⟩— | —O—CH₂— | —CH(OH)— | —S—CH₂— | —CH(OH)— |
| (CH₃)₃C—⟨C₆H₄⟩— | —O—CH₂— | —CH(OH)— | —S—CH₂— | —CH(OH)— |
| CH₃—⟨C₆H₄⟩— (para) | —O—CH₂— | —CH(OH)— | —S—CH₂— | —CH(OH)— |
| CH₃—⟨C₆H₄⟩— (meta) | —O—CH₂— | —CH(OH)— | —S—CH₂— | —CH(OH)— |
| CH₃—⟨C₆H₄⟩— (ortho) | —O—CH₂— | —CH(OH)— | —S—CH₂— | —CH(OH)— |
| FCl₂CO—⟨C₆H₄⟩— | —O—CH₂— | —CH(OH)— | —S—CH₂— | —CH(OH)— |
| ClF₂CO—⟨C₆H₄⟩— | —O—CH₂— | —C(=O)— | —O—CH₂— | —CH(OH)— |
| FCl₂CS—⟨C₆H₄⟩— | —O—CH₂— | —C(=O)— | —O—CH₂— | —CH(OH)— |
| CF₃—O,O-benzodioxole | —O—CH₂— | —C(=O)— | —O—CH₂— | —CH(OH)— |
| CHF₂—O,O-benzodioxole | —O—CH₂— | —C(=O)— | —O—CH₂— | —CH(OH)— |
| CF₃—O,O-benzodioxole (F-substituted) | —O—CH₂— | —C(=O)— | —O—CH₂— | —CH(OH)— |

-continued $$Ar-X-\underset{\underset{CH_3}{|}}{\overset{\overset{CH_3}{|}}{C}}-Y-\underset{}{\overset{}{\underset{N}{\diagdown}\underset{}{\diagup}\overset{N}{\diagup}}}$$ (I)

| Ar | X | Y | X | Y |
|---|---|---|---|---|
| 2,3-dimethyl-phenyl with OCF₂CHF₂ | —O—CH₂— | —C(=O)— | —O—CH₂— | —CH(OH)— |
| phenyl with OCF₂CF₃ | —O—CH₂— | —C(=O)— | —O—CH₂— | —CH(OH)— |
| 4-Cl-phenyl | —O—CH₂—CH₂— | —C(=O)— | —O—CH₂—CH₂— | —CH(OH)— |
| 2,4-Cl₂-phenyl | —O—CH₂—CH₂— | —C(=O)— | —O—CH₂—CH₂— | —CH(OH)— |
| 4-F-phenyl | —O—CH₂—CH₂— | —C(=O)— | —O—CH₂—CH₂— | —CH(OH)— |
| 2,4-F₂-phenyl | —O—CH₂—CH₂— | —C(=O)— | —O—CH₂—CH₂— | —CH(OH)— |
| 2-F-4-CF₃-phenyl | —O—CH₂—CH₂— | —C(=O)— | —O—CH₂—CH₂— | —CH(OH)— |
| 4-(ClF₂CO)-phenyl | —S—CH₂— | —C(=O)— | —S—CH₂— | —CH(OH)— |
| 4-(FCl₂CS)-phenyl | —S—CH₂— | —C(=O)— | —S—CH₂— | —CH(OH)— |
| phenyl with OCF₂CF₃ (dioxole) | —S—CH₂— | —C(=O)— | —S—CH₂— | —CH(OH)— |
| phenyl with OCHF₂ dioxole | —S—CH₂— | —C(=O)— | —S—CH₂— | —CH(OH)— |

-continued $$\text{Ar}-X-\underset{\underset{CH_3}{|}}{\overset{\overset{CH_3}{|}}{C}}-Y-\underset{}{\overset{}{\underset{N}{\overset{N}{\diagup\hspace{-0.3em}\diagdown}}}}$$ (I)

| Ar | X | Y | X | Y |
|---|---|---|---|---|
| 2,2,2-trifluoroethoxy-phenyl (benzodioxin-type) | —S—CH₂— | —C(=O)— | —S—CH₂— | —CH(OH)— |
| 2,2,2-trifluoroethoxy-phenyl isomer | —S—CH₂— | —C(=O)— | —S—CH₂— | —CH(OH)— |
| tetrafluoro-benzodioxin-phenyl | —S—CH₂— | —C(=O)— | —S—CH₂— | —CH(OH)— |
| 4-Cl-phenyl | —S—CH₂—CH₂— | —C(=O)— | —S—CH₂—CH₂— | —CH(OH)— |
| 2,4-Cl₂-phenyl | —S—CH₂—CH₂— | —C(=O)— | —S—CH₂—CH₂— | —CH(OH)— |
| 4-F-phenyl | —S—CH₂—CH₂— | —C(=O)— | —S—CH₂—CH₂— | —CH(OH)— |
| 2,4-F₂-phenyl | —S—CH₂—CH₂— | —C(=O)— | —S—CH₂—CH₂— | —CH(OH)— |
| 2-F-4-CF₃-phenyl | —S—CH₂—CH₂— | —C(=O)— | —S—CH₂—CH₂— | —CH(OH)— |
| 4-Br-phenyl | —O—CH₂—CH₂— | —C(=O)— | —O—CH₂—CH₂— | —CH(OH)— |
| 4-(CH₃ON=CH)-phenyl | —O—CH₂—CH₂— | —C(=O)— | —O—CH₂—CH₂— | —CH(OH)— |
| 2-Cl-phenyl | —O—CH₂—CH₂— | —C(=O)— | —O—CH₂—CH₂— | —CH(OH)— |

-continued $$Ar-X-\underset{\underset{CH_3}{|}}{\overset{\overset{CH_3}{|}}{C}}-Y-\underset{N}{\overset{N}{\diagdown}}\quad (I)$$

| Ar | X | Y | X | Y |
|---|---|---|---|---|
| 3-Cl-C6H4- | −O−CH2−CH2− | −C(=O)− | −O−CH2−CH2− | −CH(OH)− |
| 2-F-C6H4- | −O−CH2−CH2− | −C(=O)− | −O−CH2−CH2− | =CH−OH |
| 3-F-C6H4- | −O−CH2−CH2− | −C(=O)− | −O−CH2−CH2− | −CH(OH)− |
| 4-F3CO-C6H4- | −O−CH2−CH2− | −C(=O)− | −O−CH2−CH2− | −CH(OH)− |
| 4-F3CS-C6H4- | −O−CH2−CH2− | −C(=O)− | −O−CH2−CH2− | −CH(OH)− |
| 4-F3C-C6H4- | −O−CH2−CH2− | −C(=O)− | −O−CH2−CH2− | −CH(OH)− |
| 3,5-Cl2-C6H3- | −O−CH2−CH2− | −C(=O)− | −O−CH2−CH2− | −CH(OH)− |
| 3,4-Cl2-C6H3- | −O−CH2−CH2− | −C(=O)− | −O−CH2−CH2− | −CH(OH)− |
| 4-CH3O-C6H4- | −O−CH2−CH2− | −C(=O)− | −O−CH2−CH2− | −CH(OH)− |
| 4-Br-C6H4- | −S−CH2−CH2− | −C(=O)− | −S−CH2−CH2− | −CH(OH)− |
| 4-(CH3ON=CH)-C6H4- | −S−CH2−CH2− | −C(=O)− | −S−CH2−CH2− | −CH(OH)− |

-continued $$Ar-X-\underset{\underset{CH_3}{|}}{\overset{\overset{CH_3}{|}}{C}}-Y-\underset{N}{\overset{N}{\diagdown}}\hspace{-2pt}\diagup \qquad \text{(I)}$$

| Ar | X | Y | X | Y |
|---|---|---|---|---|
| 2-Cl-C6H4- | −S−CH2−CH2− | −C(=O)− | −S−CH2−CH2− | −CH(OH)− |
| 3-Cl-C6H4- | −S−CH2−CH2− | −C(=O)− | −S−CH2−CH2− | −CH(OH)− |
| 2-F-C6H4- | −S−CH2−CH2− | −C(=O)− | −S−CH2−CH2− | −CH(OH)− |
| 3-F-C6H4- | −S−CH2−CH2− | −C(=O)− | −S−CH2−CH2− | −CH(OH)− |
| 4-F3CO-C6H4- | −S−CH2−CH2− | −C(=O)− | −S−CH2−CH2− | −CH(OH)− |
| 4-F3CS-C6H4- | −S−CH2−CH2− | −C(=O)− | −S−CH2−CH2− | −CH(OH)− |
| 4-F3C-C6H4- | −S−CH2−CH2− | −C(=O)− | −S−CH2−CH2− | −CH(OH)− |
| 3,5-Cl2-C6H3- | −S−CH2−CH2− | −C(=O)− | −S−CH2−CH2− | −CH(OH)− |
| 3,4-Cl2-C6H3- | −S−CH2−CH2− | −C(=O)− | −S−CH2−CH2− | −CH(OH)− |
| 4-CH3O-C6H4- | −S−CH2−CH2− | −C(=O)− | −S−CH2−CH2− | −CH(OH)− |

-continued $$Ar-X-\underset{\underset{CH_3}{|}}{\overset{\overset{CH_3}{|}}{C}}-Y-\left[\begin{array}{c}\text{pyrimidine}\end{array}\right] \quad (I)$$

| Ar | X | Y | X | Y |
|---|---|---|---|---|
| 3-CH₃O-C₆H₄- | -O-CH₂-CH₂- | -C(=O)- | -O-CH₂-CH₂- | -CH(OH)- |
| 2-CH₃O-C₆H₄- | -O-CH₂-CH₂- | -C(=O)- | -O-CH₂-CH₂- | -CH(OH)- |
| 4-CH₃-C₆H₄- | -O-CH₂-CH₂- | -C(=O)- | -O-CH₂-CH₂- | -CH(OH)- |
| 3-CH₃-C₆H₄- | -O-CH₂-CH₂- | -C(=O)- | -O-CH₂-CH₂- | -CH(OH)- |
| 2-CH₃-C₆H₄- | -O-CH₂-CH₂- | -C(=O)- | -O-CH₂-CH₂- | =CH(OH) |
| 4-(CH₃)₃C-C₆H₄- | -O-CH₂-CH₂- | -C(=O)- | -O-CH₂-CH₂- | -CH(OH)- |
| 4-NC-C₆H₄- | -O-CH₂-CH₂- | -C(=O)- | -O-CH₂-CH₂- | -CH(OH)- |
| 4-FCl₂CO-C₆H₄- | -O-CH₂-CH₂- | -C(=O)- | -O-CH₂-CH₂- | -CH(OH)- |
| 4-ClF₂CO-C₆H₄- | -O-CH₂-CH₂- | -C(=O)- | -O-CH₂-CH₂- | -CH(OH)- |
| 4-FCl₂CS-C₆H₄- | -O-CH₂-CH₂- | -C(=O)- | -O-CH₂-CH₂- | -CH(OH)- |
| 2-Cl-4-F₃CO-C₆H₃- | -O-CH₂-CH₂- | -C(=O)- | -O-CH₂-CH₂- | -CH(OH)- |

-continued $$Ar-X-\underset{\underset{CH_3}{|}}{\overset{\overset{CH_3}{|}}{C}}-Y-\underset{N}{\overset{N}{\diagdown}}\!\!\!\diagup \quad (I)$$

| Ar | X | Y | X | Y |
|---|---|---|---|---|
| 4-F₂CHO-C₆H₄- | -O-CH₂-CH₂- | -C(=O)- | -O-CH₂-CH₂- | -CH(OH)- |
| 4-F₂CHS-C₆H₄- | -O-CH₂-CH₂- | -C(=O)- | -O-CH₂-CH₂- | -CH(OH)- |
| 3-CH₃O-C₆H₄- | -S-CH₂-CH₂- | -C(=O)- | -S-CH₂-CH₂- | -CH(OH)- |
| 2-CH₃O-C₆H₄- | -S-CH₂-CH₂- | -C(=O)- | -S-CH₂-CH₂- | -CH(OH)- |
| 4-CH₃-C₆H₄- | -S-CH₂-CH₂- | -C(=O)- | -S-CH₂-CH₂- | -CH(OH)- |
| 3-CH₃-C₆H₄- | -S-CH₂-CH₂- | -C(=O)- | -S-CH₂-CH₂- | -CH(OH)- |
| 2-CH₃-C₆H₄- | -S-CH₂-CH₂- | -C(=O)- | -S-CH₂-CH₂- | -CH(OH)- |
| 4-(CH₃)₃C-C₆H₄- | -S-CH₂-CH₂- | -C(=O)- | -S-CH₂-CH₂- | -CH(OH)- |
| 4-NC-C₆H₄- | -S-CH₂-CH₂- | -C(=O)- | -S-CH₂-CH₂- | -CH(OH)- |
| 4-FCl₂CO-C₆H₄- | -S-CH₂-CH₂- | -C(=O)- | -S-CH₂-CH₂- | -CH(OH)- |
| 4-ClF₂CO-C₆H₄- | -S-CH₂-CH₂- | -C(=O)- | -S-CH₂-CH₂- | -CH(OH)- |

-continued

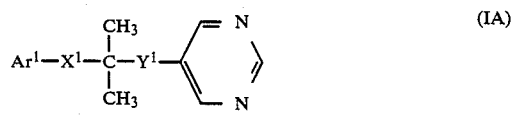

| Ar | X | Y | X | Y |
|---|---|---|---|---|
| FCl₂CS—⟨phenyl⟩— | —S—CH₂—CH₂— | —C(=O)— | —S—CH₂—CH₂— | —CH(OH)— |
| (3-Cl, 4-F₃CO)—⟨phenyl⟩— | —S—CH₂—CH₂— | —C(=O)— | —S—CH₂—CH₂— | —CH(OH)— |
| F₂CHO—⟨phenyl⟩— | —S—CH₂—CH₂— | —C(=O)— | —S—CH₂—CH₂— | —CH(OH)— |
| F₂CHS—⟨phenyl⟩— | —S—CH₂—CH₂— | —C(=O)— | —S—CH₂—CH₂— | —CH(OH)— |

Some of the substituted pyrimidines of the formula (I) which can be used according to the invention have been disclosed in German DE-OS 3,431,689 corresponding to U.S. Ser. No. 769,639 filed on Aug. 26, 1985, pending. Compounds of the formula (IA)

$$Ar^1-X^1-\underset{CH_3}{\underset{|}{\overset{CH_3}{\overset{|}{C}}}}-Y^1-\text{(pyrimidin-5-yl)} \quad (IA)$$

in which $Ar^1$ represents optionally substituted phenyl, $X^1$ represents oxygen, sulphur, sulphinyl, sulphonyl or one of the groups —CH₂—; —O—CH₂—; —CH₂—O—; —O—CH₂—CH₂—; —S(O)ₙ—CH₂—; —CH₂—S(O)ₙ— or —S(O)ₙ—CH₂—CH₂—, and $Y^1$ represents one of the groups

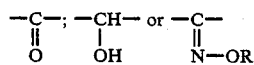

where

R represents hydrogen, alkyl, alkenyl, alkinyl or optionally substituted aralkyl, and n represents a number 0, 1 or 2, have not yet been disclosed, apart from the compounds, 2,2-dimethyl-3-(4-fluorophenyl)-1-(pyrimidin-5-yl)-propan-1-one, 2,2-dimethyl-3-(3-chlorophenoxy)-1-(pyrimidin-5-yl)-propan-1-one, 2,2-dimethyl-2-(4-chlorophenoxy)-1-(pyrimidin-5-yl)-ethan-1-one and 2,2-dimethyl-3-(4-chlorophenylthio)-1-(pyrimidin-5-yl)-propan-1-one.

Formula (IA) provides a general definition of the substituted pyrimidines according to the invention. Preferred compounds of the formula (IA) are those in which $Ar^1$ represents phenyl which is optionally monosubstituted to polysubstituted by identical or different substituents, suitable substituents being: halogen, cyano, nitro and in each case straight-chain or branched alkyl, alkoxy, alkylthio, alkylsulphinyl or alkylsulphonyl in each case having 1 to 4 carbon atoms, in each case straight-chain or branched halogenoalkyl, halogenoalkoxy, halogenoalkylthio, halogenoalkylsulphinyl or halogenoalkylsulphonyl in each case having 1 to 4 carbon atoms and 1 to 9 identical or different halogen atoms, in each case straight-chain or branched alkoxycarbonyl or alkoximinoalkyl in each case having 1 to 4 carbon atoms in the individual alkyl parts, doubly linked dioxyalkylene which is optionally monosubstituted to polysubstituted by identical or different halogen, or phenyl or phenoxy which is in each case optionally monosubstituted to polysubstituted by identical or different halogen, $X^1$ represents oxygen, sulphur, sulphinyl, sulphonyl or one of the groups —CH₂—; —O—CH₂—; —CH₂—O—; —O—CH₂—CH₂—; —S(O)ₙ—CH₂—; —CH₂—S(O)ₙ or —S(O)ₙ—CH₂—CH₂—, and $Y^1$ represents one of the groups

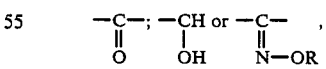

where

R represents hydrogen or in each case straight-chain or branched alkyl having 1 to 6 carbon atoms, alkenyl having 3 to 5 carbon atoms or alkinyl having 3 to 5 carbon atoms, or benzyl or phenylethyl which is in each case optionally monosubstituted to polysubstituted by identical or different substituents, suitable substituents in the phenyl part in each case being those mentioned in the case of the $Ar^1$ radical, and n represents a number 0, 1 or 2, apart from the compounds 2,2-dimethyl-3-(4-fluorophenyl)-1-(pyrimidin-5-yl)-propan-1-one, 2,2-dimethyl-3-(3-chlorophenoxy)-1-(primidin-5-yl)-propan-1-one, 2,2-dimethyl-2-(4-chlorophenoxy)-1-(pyrimidin-5-yl)-ethan)1-one and 2,2-dimethyl-3-(4-chlorophenylthio)-1-(pyrimidin-5-yl)-propan-1-one.

Particularly preferred compounds of the formula (IA) according to the invention are those in which Ar represents phenyl which is optionally monosubstituted, disubstituted or trisubstituted by identical or different substituents, suitable substituents being: fluorine, chlorine, bromine, cyano, nitro, methyl, ethyl, n- or i-propyl, n-, i-, s-or t-butyl, methoxy, ethoxy, n- or i-propoxy, methylthio, ethylthio, trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethoxy, difluoromethoxy, fluoromethoxy, dichlorofluoromethoxy, difluorochloromethoxy, difluorobromomethoxy, trichloromethoxy, trifluoroethoxy, tetrafluoroethoxy, pentafluoroethoxy, trifluorochloroethoxy, trifluorodichloroethoxy, difluorotrichloroethoxy, pentachloroethoxy, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochlorethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethylsulphonyl, dichlorofluoromethylsulphonyl, difluorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, difluorodioxymethylene, tetrafluorodioxyethylene, trifluorodioxyethylene, difluorodioxyethylene, dioxymethylene or dioxyethylene, or phenyl or phenoxy which is in each case optionally monosubstituted, disubstituted or trisubstituted by fluorine or chlorine, X represents oxygen, sulphur, sulphinyl, sulphonyl or one of the groups —CH₂—; —O—CH₂—; —CH₂—O—: —O—CH₂—CH₂—; —S(O)$_n$—CH₂—; —CH₂—S(O)$_n$— or —S(O)$_n$—CH₂—CH₂—, and Y represents one of the groups

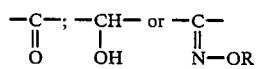

where

R represents hydrogen, methyl, ethyl, n- or i-propyl, allyl or propargyl, or benzyl which is optionally monosubstituted, disubstituted or trisubstituted by identical or different substituents, suitable substituents being those mentioned in the case of the Ar radical, and n represents a number 0, 1 or 2, apart from the compounds 2,2-dimethyl-3-(4-fluorophenyl)-1-(pyrimidin-5-yl)-propan-1-one, 2,2-dimethyl-3-(3-chlorophenoxy)-1-(pyrimidin-5-yl)-propan-1-one, 2,2-dimethyl-2-(4-chlorophenoxy)-1-(pyrimidin-5-yl)-ethan-1-one and 2,2-dimethyl-3-(4-chlorophenyl-thio)-1-(pyrimidin-5-yl)-propan-1-one.

The known compounds and the new compounds are obtained by analogous processes.

Thus, the substituted pyrimidines of the formula (IA)

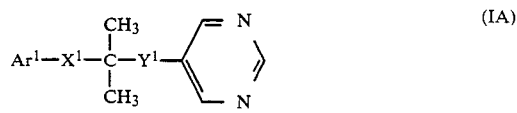

in which

Ar¹ represents optionally substituted phenyl,

X¹ represents oxygen, sulphur, sulphinyl, sulphonyl or one of the groups —CH₂—; —O—CH₂—; —CH₂—O—; —O—CH₂—CH₂—; —S(O)$_n$—CH₂—; —CH₂—S(O)$_n$— or —S(O)$_n$—CH₂—CH₂—, and Y¹ represents one of the groups

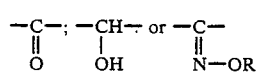

where

R represents hydrogen, alkyl, alkenyl, alkinyl or optionally substituted aralkyl, and n represents a number 0, 1 or 2, apart from the compounds 2,2-dimethyl-3-(4-fluorophenyl)-1-(pyrimider-5-yl)-propan-1-one, 2,2-dimethyl-3-(3-chlorophenoxy)-1-(pyrimidin-5-yl)-propan-1-one, 2,2-dimethyl-2-(4-chlorophenoxy)-1-(pyrimidin-5-yl)-ethan-1-one and 2,2-dimethyl-3-(4-chlorophenylthio)-1-(pyrimidin-5-yl)-propan-1-one, which have not yet been disclosed, and the acid-addition salts and metal salt complexes thereof, are obtained analogously to known methods by the processes shown below:

(a) Substituted pyrimidines of the formula (Ia)

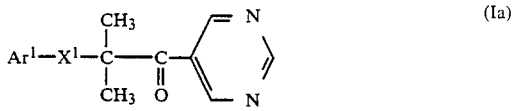

in which Ar¹ and X¹ have the abovementioned meaning, are obtained when acylenols of the formula (II)

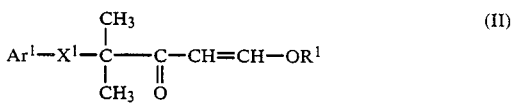

in which

Ar¹ and X¹ have the abovementioned meaning, and

R¹ represents hydrogen or an alkali metal cation, are reacted successively with formamidine or an acid-addition salt of formamidine, such as, for example, formamidine hydroacetate, and then with formaldehyde dimethyl acetate, if appropriate in the presence of a diluent;

(b) substituted pyrimidines of the formula (Ib)

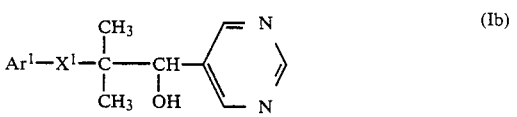

in which Ar¹ and X¹ have the abovementioned meaning, are obtained when the substituted pyrimidines of the formula (Ia)

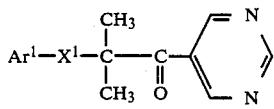 (Ia)

in which Ar¹ and X¹ have the abovementioned meaning, obtainable by process (a) or (d) are reacted with a reducing agent, if appropriate in the presence of a diluent;

(c) substituted pyrimidines of the formula (Ic)

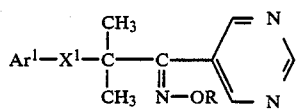 (Ic)

in which Ar¹, X¹ and R have the abovementioned meaning, are obtained when the substituted pyrimidines of the formula (Ia)

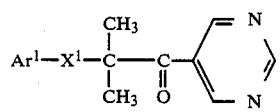 (Ia)

in which Ar¹ and X¹ have the abovementioned meaning, obtainable by process (a) or (d) are reacted with hydroxylamines of the formula (III)

R—O—NH₂ (III)

in which R has the abovementioned meaning, or with the acid-addition salts thereof, if appropriate in the presence of a diluent and if appropriate in the presence of an acid-binding agent;

(d) substituted pyrimidines of the formula (Id)

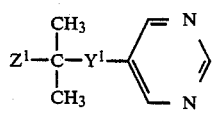 (Id)

in which $Z^1$ represents and $Ar^1$—$X^2$— radical or an $Ar^2$—$X^1$— radical, where Ar¹, X¹ and Y¹ have the abovementioned meaning, Ar² represents a phenyl radical which is substituted by alkylsulphinyl, alkylsulphonyl, halogenoalkylsulphinyl or halogenoalkylsulphonyl, $X^2$ represents sulphinyl, sulphonyl or one of the groups —S(O)$_m$—CH₂—; —CH₂—S(O)$_m$— or —S(O)-$_m$—CH₂—CH₂—, and m represents a number 1 or 2, are obtained when the substituted pyrimidines of the formula (Ie)

 (Ie)

in which $Z^2$ represents an $Ar^1$—$X^3$— radical or an $Ar^3$—$X^1$— radical, where Ar¹, X¹ and Y¹ have the abovementioned meaning, Ar³ represents a phenyl radical which is substituted by alkylthio or halogenoalkylthio, and $X^3$ represents sulphur or one of the groups —S—CH₂—; —CH₂—S— or —S—CH₂—CH₂—, obtainable by process (a), (b) or (c) are reacted with an oxidant, if appropriate in the presence of a diluent and if appropriate in the presence of a reaction auxiliary, and, if appropriate, an acid or metal salt is added to the compounds obtainable with the aid of preparation processes (a), (b), (c) or (d).

If, for example, the sodium salt of 4,4-dimethyl-5-(4-trifluoromethylthiophenyl)-1-penten-1-ol-3-one is used as the starting compound, the course of the reaction of preparation process (a) may be represented by the following equation:

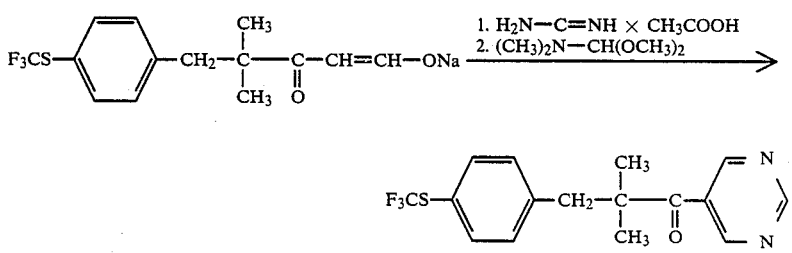

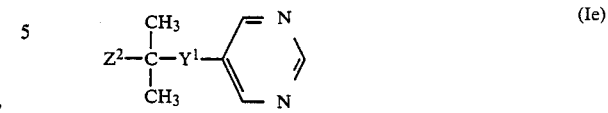

If, for example, 1-(5-pyrimidyl)-2,2-dimethyl-3-(4-trifluoromethylthiophenyl)-propan-1-one is used as the starting compound and sodium borohydride is used as the reducing agent, the course of the reaction of preparation process (b) may be represented by the following equation:

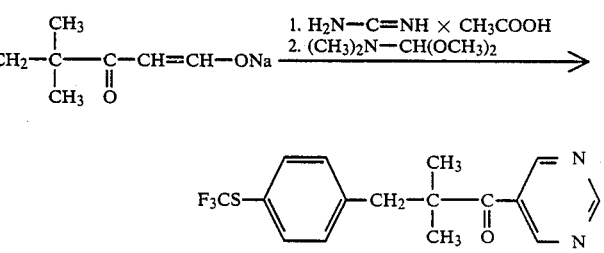

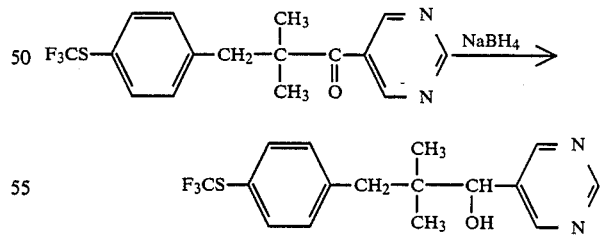

If, for example, 1-(5-pyrimidyl)-2,2-dimethyl-3-(4-trifluoromethylphenyl)-propane-1-one and 0-methylhydroxylamine hydrochloride are used as starting materials, the course of the reaction of preparation process (c) may be represented by the following equation:

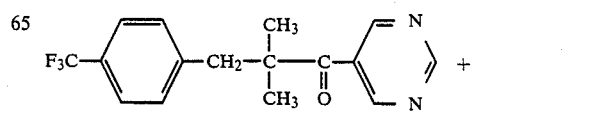

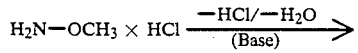

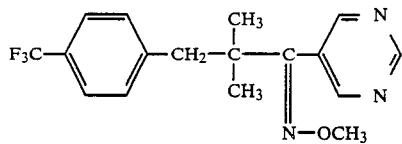

If, for example, 1-(5-pyrimidyl)-2,2-dimethyl-3-(4-tri-fluoromethylthiophenyl)-propan-1-ol is used as the starting compound and hydrogen peroxide is used as the oxidant, the course of the reaction of preparation process (d) may be represented by the following equation:

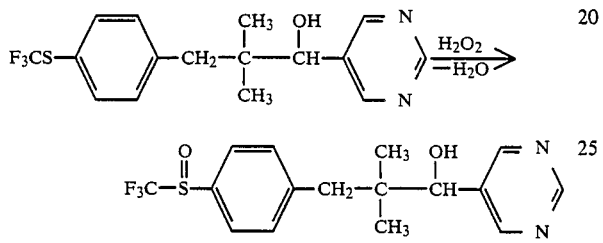

Formula (II) provides a general definition of the acylenols required as starting materials for carrying out preparation process (a). In this formula (II), Ar$^1$ and X$^1$ preferably represent those radicals which have already been mentioned in connection with the description of the substances of the formula (I) which can be used according to the invention as being preferred for substituents Ar and X.

Some of the acylenols of the formula (II) are known or can be obtained analogously to known processes (cf., for example, German DE-OS 3,431,689 corresponding to U.S. Ser. No. 769,639 filed on Aug. 26, 1985, pending), for example when ketones of the formula (IV)

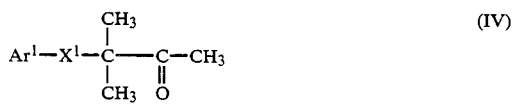

in which

Ar$^1$ and X$^1$ have the abovementioned meaning, are reacted with ethyl formate, if appropriate in the presence of a base, such as, for example, sodium ethylate or sodium methylate, and if appropriate in the presence of a diluent, such as, for example, diethyl ether, at temperatures between −20° C. and +60° C.

The ketones of the formula (IV) are known (cf., for example, DE-OS (German Published Specification) 3,210,725 or DE-OS (German Published Specification) 3,048,266) or can be prepared analogously to known processes.

Formula (Ia) provides a general definition of the substituted pyrimidines required as starting materials for carrying out preparation processes (b) and (c). In this formula (Ia), Ar$^1$ and X$^1$ preferably represent those radicals which have already been mentioned in connection with the description of the substances of the formula (I) which can be used according to the invention as being preferred for substituents Ar and X, apart from the compounds 2,2-dimethyl-3-(4-fluorophenyl)-1-(pyrimidin-5-yl)-propan-1-one, 2,2-dimethyl-3-(3-chlorophenoxy)-1-(pyrimidin-5-yl)-propan-1-one, 2,2-dimethyl-2-(4-chlorophenoxy)-1-(pyrimidin-5-yl)-ethan-1-one and 2,2-dimethyl-3-(4-chlorophenylthio)-1-(pyrimidin-5-yl)-propan-1-one.

The substituted pyrimidines of the formula (Ia) are compounds according to the invention and can be obtained with the aid of preparation processes (a) or (d).

Formula (III) provides a general definition of the hydroxylamines furthermore required as starting materials for carrying out preparation process (c). In this formula (III), R preferably represents those radicals which have already been mentioned in connection with the description of the substances of the formula (I) which can be used according to the invention as being preferred for this substituent. Preferred acid-addition salts of the hydroxylamines of the formula (III) are hydrohalides, such as, in particular, hydrochlorides or hydrobromides. The hydroxylamines of the formula (III) and the acid-addition salts thereof, such as hydrochlorides or hydrobromides, are generally known compounds.

Formula (Ie) provides a general definition of the substituted pyrimidines required as starting materials for carrying out preparation process (d). In this formula (Ie), X$^1$ preferably represents those radicals which have already been mentioned in connection with the description of the substances of the formula (I) which can be used according to the invention as being preferred for this substituent.

Z$^2$ represents an Ar$^1$—X$^3$— or an Ar$^3$—X$^1$— radical, where Ar$^1$ and X$^1$ preferably represent those radicals which have already been mentioned in connection with the description of the substances of the formula (I) which can be used according to the invention as being preferred for these substituents, apart from the compounds 2,2-dimethyl-3-(4-fluorophenyl)-1-(pyrimidin-5-yl)-propan-1-one, 2,2-dimethyl-3-(3-chlorophenoxy)-1-(pyrimidin-5-yl)-propan-1-one, 2,2-dimethyl-2-(4-chlorophenoxy)-1-(pyrimidin-5-yl)-ethan-1-one and 2,2-dimethyl-3-(4-chlorophenylthio)-1-(pyrimidin-5-yl)-propan-1-one.

Ar$^3$ preferably represents a phenyl radical which is monosubstituted to polysubstituted by in each case straight-chain or branched alkylthio or halogenoalkylthio in each case having 1 to 4 carbon atoms and, if appropriate, 1 to 9 identical or different halogen atoms. Particularly preferred phenyl substituents here are methylthio, ethylthio, trifluoromethylthio, difluoromethylthio, fluoromethylthio, difluorochloromethylthio, dichlorofluoromethylthio, difluorobromomethylthio, trichloromethylthio, trifluoroethylthio, tetrafluoroethylthio, pentafluoroethylthio, trifluorochloroethylthio, trifluorodichloroethylthio or pentachloroethylthio;

X$^3$ preferably represents sulphur or one of the groups —CH$_2$—S—; —S—CH$_2$— or —S—CH$_2$—CH$_2$—.

The substituted pyrimidines of the formula (Ie) are compounds according to the invention and can be obtained with the aid of preparation processes (a), (b) or (c).

Suitable diluents for carrying out preparation process (a) are inert organic solvents. Aprotic solvents, such as, for example, ethers, in particular diethyl ether, diisopropyl ether, 1,2-dimethoxyethane or tetrahydrofuran, or aromatic or aliphatic hydrocarbons, such as benzene, toluene, xylene, petroleum ether, hexane, cyclohexane or octane, are preferably used.

The reaction temperatures may be varied within a relatively wide range when carrying out preparation process (a). In general, the process is carried out at temperatures between −25° C. and +100° C., preferably at temperatures between 0° C. and 80° C.

In order to carry out preparation process (a), 1.0 to 2.0 moles, preferably 1.0 to 1.5 moles, of formamidine or an acid-addition salt of formamidine, such as, for example, formamidine hydroacetate, and 1.0 to 2.0 moles, preferably 1.0 to 1.5 moles, of dimethylformamide dimethyl acetal are generally employed per mole of acylenol of the formula (II). The reaction is carried out and the reaction products of the formula (Ia) are worked up and isolated analogously to known processes in German DE-OS 3,431,689 corresponding to U.S. Ser. No. 769,639 filed on Aug. 26, 1985, pending.

Suitable reducing agents for carrying out preparation process (b) are all conventional reducing agents which are customary for such ketone reductions. Complex hydrides, such as, for example, lithium aluminum hydride, sodium borohydride or sodium cyanoborohydride, or organoaluminium compounds, such as, for example, aluminum isopropylate, are preferably used.

Suitable diluents for carrying out preparation process (b) are inert organic solvents. Hydrocarbons, such as benzene or toluene; ethers, such as diethyl ether or tetrahydrofuran, or alcohols, such as methanol, ethanol, n- or i-propanol and n- or i-butanol, are preferably used.

The reaction temperatures may be varied within a relatively wide range when carrying out preparation process (b). In general, the process is carried out at temperatures between −20° C. and +120° C., preferably at temperatures between 0° C. and 80° C.

In order to carry out preparation process (b), 0.25 mole to 2 moles, preferably equimolar amounts, of reducing agent are generally employed per mole of the substituted pyrimidine of the formula (Ia). The reaction is carried out and the reaction products of the formula (Ib) are worked up and isolated by generally known methods.

The carbinols of the formula (Ib) according to the invention which can be obtained with the aid of preparation process (b) are, in addition, also important intermediates for the preparation of other plant-protection active compounds. They can be derivatized at the hydroxyl group in a generally known fashion, for example converted into the corresponding ethers with the aid of a "Williamson ether synthesis" or converted into the corresponding esters or carbamates by reaction with acyl halides or carbamoyl halides.

Suitable diluents for carrying out preparation process (c) are polar organic solvents or mixtures thereof with water. Alcohols, such as methanol, ethanol or propanol, or mixtures thereof with water, are preferably used.

Preparation process (c) can be carried out, if appropriate, in the presence of a suitable acid-binding agent.

Suitable acid-binding agents are all conventional inorganic or organic bases. These include, for example, alkali metal hydroxides, such as sodium hydroxide or potassium hydroxide, alkali metal carbonates or acetates, such as sodium carbonate, potassium carbonate or sodium hydrogen carbonate or sodium acetate, and also tertiary amines, such as triethylamine, N,N-dimethylaniline, pyridine, N,N-dimethylaminopyridine, diazabicyclooctane (DABCO), diazabicyclononene (DBN) or diazabicycloundecane (DBU).

The reaction temperatures may be varied within a relatively wide range when carrying out preparation process (c). In general, the process is carried out at temperatures between 0° C. and 120° C. preferably at temperatures between 20° C. and 100° C.

In order to carry out preparation process (c), 1.0 to 2.0 moles, preferably 1.0 to 1.3 moles, of hydroxylamine of the formula (III), preferably in the form of the corresponding hydrochloride, and 1.0 to 2.0 moles, preferably 1.0 to 1.3 moles, of acid-binding agent are generally employed per mole of the substituted pyrimidine of the formula (Ia). The reaction is carried out and the reaction products of the formula (Ie) are worked up and isolated by generally known methods.

Suitable oxidants for carrying out preparation process (d) are all oxidants which can conventionally be used for sulphur oxidations. Hydrogen peroxide or organic peracids, such as, for example, peracetic acid, 4-nitroperbenzoic acid or 3-chloroperbenzoic acid, or alternatively inorganic oxidants, such as periodic acid, potassium permanganate or chromic acid, are preferably used.

Suitable diluents for carrying out preparation process (d) are inorganic or organic solvents, depending on the oxidant used. Alcohols, such as methanol or ethanol, or mixtures thereof with water, and also pure water; acids, such as, for example, acetic acid, acetic anhydride or propionic acid, or dipolar aprotic solvents, such as acetonitrile, acetone, ethyl acetate or dimethylformamide, and also optionally halogenated hydrocarbons, such as benzine, benzene, toluene, hexane, cyclohexane, petroleum ether, dichloromethane, dichloroethane, chloroform, carbon tetrachloride or chlorobenzene, are preferably used.

Preparation process (d) can be carried out, if appropriate, in the presence of an acid-binding agent.

Suitable acid-binding agents are all organic and inorganic acid-binding agents which can conventionally be used. Alkaline-earth metal or alkali metal hydroxides, acetates or carbonates, such as, for example, calcium hydroxide, sodium hydroxide, sodium acetate or sodium carbonate, are preferably used.

Preparation process (d) can be carried out, if appropriate, in the presence of a suitable catalyst. Suitable catalysts are all catalysts which can conventionally be used for such sulphur oxidations. Heavy-metal catalysts are preferably used; an example which may mentioned in this connection is ammonium molybdate.

The reaction temperatures may be varied within a relatively wide range when carrying out preparation process (d). In general, the process is carried out at temperatures between −30° C. and +100° C., preferably at temperatures between 0° C. and +80° C.

In order to carry out preparation process (d), 0.8 to 1.2 moles, preferably equimolar amounts, of oxidant are generally employed per mole of the substituted pyrimidine of the formula (Ie) if it is desired that the oxidation of the sulphur be interrupted at the sulphoxide stage. For oxidation to the sulphone stage, 1.8 to 3.0 moles, preferably twice the molar amounts, of oxidants are generally employed per mole of the substituted pyrimidine of the formula (Ie). The reaction is carried out and the reaction products of the formula (Id) are worked up and isolated by generally known methods.

In order to prepare acid-addition salts of the compounds of the formula (I) which are tolerated by plants, the following acids are preferably suitable: hydrohalic acids, such as, for example, hydrochloric acid and hydrobromic acid, in particular hydrochloric acid, furthermore phosphoric acid, nitric acid, sulphuric acid, mono-, bi-and trifunctional carboxylic acids and hydroxycarboxylic acids, such as, for example, acetic acid, maleic acid, succinic acid, fumaric acid, tartaric acid, citric acid, salicylic acid, sorbic acid, lactic acid, thus such as sulphonic acids, such as, for example, p-toluenesulphonic acid and 1,5-naphthalenedisulphonic acid.

The acid-addition salts of the compounds of the formula (I) can be obtained in a simple fashion by conventional salt-formation methods, such as, for example, by dissolving a compound of the formula (I) in a suitable inert solvent and adding the acid, such as, for example, hydrochloric acid, and can be isolated in a known fashion, for example by filtering off, and purified, if appropriate, by washing with an inert organic solvent.

For the preparation of metal-salt complexes of the compounds of the formula (I), salts of metals of main group II to IV and subgroup I and II and IV to VIII are preferably suitable, where copper, zinc, manganese, magnesium, tin, iron and nickel may be mentioned as examples.

Possible anions of salts are those which are preferably derived from the following acids: hydrohalic acid, such as, for example, hydrochloric acid and hydrobromic acid, furthermore phosphoric acid, nitric acid and sulphuric acid.

The metal-salt complexes of compounds of the formula (I) can be obtained in a simple fashion by conventional processes, thus, for example, by dissolving the metal salt in alcohol, for example ethanol, and adding to the compound of the formula (I). Metal-salt complexes can be isolated in a known fashion, for example by filtering off, and purified, if appropriate, by recrystallization.

The active compounds which can be used according to the invention have a strong action against pests and can be employed in practice for combating undesired harmful organisms. The active compounds are suitable, inter alia, for use as plant-protection agents, in particular as fungicides and bactericides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some pathogens of fungal and bacterial diseases which come under the generic names listed above may be mentioned as examples, but not by way of limitation: Xanthomonas species, such as, for example, *Xanthomonas campestris pv. oryzae;* Pseudomonas species, such as, for example, *Pseudomonas syringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera Leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such, as, for example, *Fusarium culmorum;* botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds which can be used according to the invention can be employed particularly successfully here for combating cereal diseases such as, for example, against the pathogen of glume blotch in wheat (*Leptosphaeria nodorum*) or against the pathogen of net blotch in barley (*Pyrenophora teres*) or against the pathogen of brown spot disease in cereals (*Cochliobolus sativus*), against mildew and rust species, and also for combating diseases in vegetable and fruit growing, such as, for example, against the pathogen of applescab (*Venturia inaequalis*) and against Botrytis species, and for combating rice diseases, such as, for example, against the pathogen of rice spot disease (*Pyricularis oryzae*). In addition, the active compounds which can be used according to the invention also exhibit good bactericidal and plant growth-regulating properties.

Depending on their particular physical and/or chemical properites, the active compounds can be converted to the customary formulation, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic materials such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts or iron, manganese, boron, copper, cobalt, molybdenum and zinc.

The formulations in general contain between 0.1 and 95 per cent by weight of active compound, preferably between 0.5 and 90%.

The active compounds which can be used according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example be watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.001 to 0.02% by weight, are required at the place of action.

Preparation examples

Example 1:

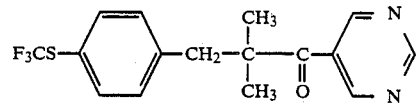

(Process a)

97.0 g (0.298 mole) of the sodium salt of 4,4-dimethyl-5-(4-trifluoromethylthiophenyl)-1-penten-1-ol-3-one and 39.0 g (0.374 mole) of formamidine hydroacetate in 500 ml of tetrahydrofuran are stirred at room temperature for 30 minutes, and 48.5 g (0.406 mole) of dimethylformamide dimethyl acetal are then added dropwise with stirring. The mixture is stirred at 50° C. to 60° C. for 6 hours, then cooled to room temperature and filtered under suction, the filtrate is concentrated in vacuo, and the residue is purified by chromatography (silica gel; diethyl ether).

18.5 g (18.3% of theory) of 1-(5-pyrimidyl)-2,2-dimethyl-3-(4-trifluoromethylthiophenyl)-propan-1-one are obtained as an oil.

$^1$H NMR (CDCl$_3$/TMS): $\delta$=1.75; 3.10; 8.89; 9.29 ppm.

Preparation of the starting compound

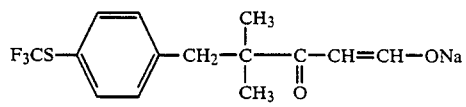

34.7 g (0.469 mole) of ethyl formate are added dropwise with stirring to 129.4 g (0.469 mole) of 3,3-dimethyl-4-(4-trifluoromethylthiophenyl)-butan-2-one and 25.3 g (0.469 mole) of sodium methylate in 1 liter of diethyl ether at room temperature, and the mixture is stirred at room temperature for 4 hours after the addition is complete. For work-up, the mixture is extracted with 1 liter of water, and the combined aqueous extracts are washed once with diethyl ether, acidified to pH 1–2 with dilute aqueous hydrochloric acid and extracted with dichloromethane. The dichloromethane phase is dried over sodium sulphate and concentrated in vacuo. 90.5 g of 4,4-dimethyl-5-(4-trifluoromethylthiophenyl)-penten-1-ol-3-one are obtained; these are dissolved in 200 ml of methanol and 17.0 g (0.315 mol) of sodium methylate are added. Concentrating the solution in vacuo gives 97.1 g (75% of theory) of the sodium salt of 4,4-dimethyl-5-(4-trifluoromethylthiophenyl)-1-penten-1-ol-3-one as a resin, which is further reacted without purification.

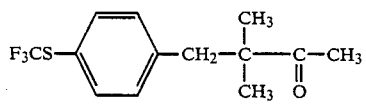

147.8 g (2.64 mole) of powdered potassium hydroxide and 8.8 g (0.027 mole) of tetrabutylammonium bromide are introduced into 270 ml of toluene at room temperature. A mixture of 200 g (0.88 mole) of 4-trifluoromethylthiobenzyl chloride and 90.9 g (1.06 mole) of methyl isopropyl ketone are run in at 20° C. to 25° C. with cooling. When the addition is complete, the mixture is stirred for a further 8 hours at 20° C. to 25° C. For work-up, 500 ml of water are added, the phases are separated, and the organic phase is dried over sodium sulphate and concentrated in a water-pump vacuum. The residue is subjected to fractional distillation.

115 g (47.3% of theory) of 3,3-dimethyl-4-(4-trifluoromethylthiophenyl)-butan-2-one of boiling point 100° C. at 0.8 mbar are obtained.

Example 2:

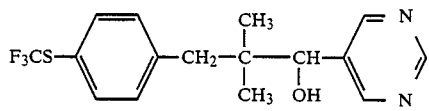

(Process b)

0.37 g (0.0098 mole) of sodium borohydride in 7 ml of water is added to 10 g (0.0294 mole) of 1-(5-pyrimidyl)-2,2-dimethyl-3-(4-trifluoromethylthiophenyl)-propan-1-one in 70 ml of methanol, and the mixture is stirred at room temperature for 30 minutes. For work-up, the mixture is concentrated in vacuo, the residue is taken up in dichloromethane, the solution is dried over sodium sulphate, and the solvent is removed in vacuo.

10.05 g (100% of theory) of 1-(5-pyrimidyl)-2,2-dimethyl-3-(4-trifluoromethylthiophenyl)-propan-1-ol of refractive index $n_D^{20}$ 1.5300 are obtained.

Example 3:

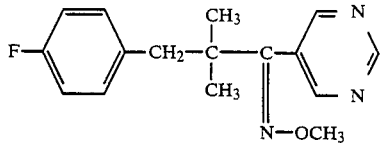

(Process c)

8.0 g (0.031 mole) of 1-(5-pyrimidinyl)-2,2-dimethyl-3-(4-fluorophenyl)-propan-1-one (cf. German DE-OS 3,431,689 corresponding to U.S. Ser. No. 769,639 filed on Aug. 26, 1985, pending) 4.0 g (0.048 mole) of O-methyl-hydroxylamine hydrochloride and 4.0 g (0.049 mole) of sodium acetate are stirred at room temperature for 15 hours in a mixture of 50 ml of methanol and 10 ml of water. For workup, the batch is diluted with 200 ml of water, and a precipitated reaction product is filtered off under suction and dissolved in methylene chloride. The methylene chloride solution is dried over sodium sulphate and concentrated in vacuo.

5.7 g (64.1% of theory) of 1-methoximin-1-(5-pyrimidinyl)-2,2-dimethyl-3-(4-fluorophenyl)-propane are obtained as an oil.

$^1$H NMR (CDCl$_3$/tetramethylsilane): $\delta = 1.10$ (s,6H); 2.86 (s,2H); 3.80 (s,3H) ppm.

Example 4:

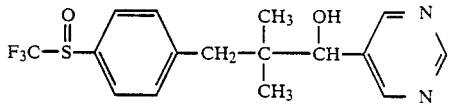

(Process d)

1.74 g (0.0174 mole) of 35 per cent aqueous hydrogen peroxide solution are added to 2 g (0.0058 mole) of 1-(5-pyrimidyl)-2,2-dimethyl-3-(4-trifluoromethylthiophenyl)propan-1-ol in 10 ml of glacial acetic acid, the mixture is stirred at 50° C. for 8 hours, cooled, stirred with 100 ml of water and extracted with dichloromethane, the dichloromethane phase is neutralized using aqueous sodium hydrogen carbonate, washed with water, dried over sodium sulphate and concentrated in vacuo, and the residue is purified by chromatography (silica gel: ethyl acetate/cyclohexane 3:1).

0.5 g (23% of theory) of 1-(5-pyrimidyl)-2,2-dimethyl-3-(4-trifluoromethylsulphinylphenyl)-propan-1-ol of melting point 122° C. are obtained.

The following substituted pyrimidines of the general formula (I) are obtained in a corresponding fashion and according to the general information on the preparation:

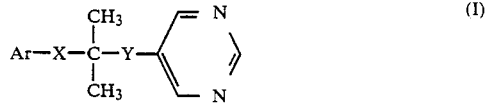

| Example No. | Ar | X | Y | Physical properties |
|---|---|---|---|---|
| 5 | Cl—⟨phenyl⟩— | O | —C(=O)— | m.p. 106° C. |
| 6 | F—⟨phenyl⟩— | —CH$_2$— | —C(=O)— | $n_D^{20}$ 1.5473 |

-continued
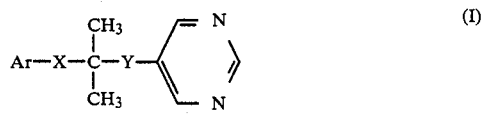
| Example No. | Ar | X | Y | Physical properties |
|---|---|---|---|---|
| 7 | 4-Cl-C6H4- | O | -CH(OH)- | m.p. 100° C. |
| 8 | 4-Cl-C6H4- | -S-CH2- | -C(=O)- | m.p. 58° C. |
| 9 | 3-Cl-C6H4- | -O-CH2- | -C(=O)- | m.p. 178° C. |
| 10 | 4-Cl-C6H4- | -CH2- | -C(=O)- | m.p. 65° C. |
| 11 | 4-Cl-C6H4- | -CH2- | -C(=N-OCH3)- | m.p. 102° C. |
| 12 | 2-Cl-C6H4- | -CH2- | -C(=O)- | 1H NMR*: 1.37 (6H) 3.25 (2H) 8.96 (2H) 9.27 (1H) |
| 13 | 4-CH3-C6H4- | -CH2- | -C(=O)- | m.p. 60° C. |
| 14 | 4-Cl-C6H4- | -CH2- | -CH(OH)- | m.p. 129° C. |
| 15 | 2-Cl-C6H4- | -CH2- | -C(=N-OCH3)- | m.p. 74° C. |
| 16 | 4-CH3-C6H4- | -CH2- | -C(=N-OCH3)- | m.p. 74° C. |
| 17 | 2-Cl-C6H4- | -CH2- | -CH(OH)- | m.p. 110° C. |

-continued
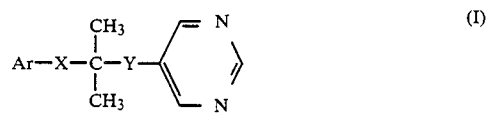
(I)
| Example No. | Ar | X | Y | Physical properties |
|---|---|---|---|---|
| 18 | 4-F-C6H4- | —CH2— | —CH(OH)— | m.p. 115° C. |
| 19 | 3,4-Cl2-C6H3- | —CH2— | —C(=O)— | m.p. 105° C. |
| 20 | 3,4-Cl2-C6H3- | —CH2— | —CH(OH)— | m.p. 107° C. |
| 21 | 2,4-Cl2-C6H3- | —CH2— | —C(=O)— | m.p. 99° C. |
| 22 | 2,4-Cl2-C6H3- | —O—CH2— | —C(=O)— | m.p. 44° C. |
| 23 | 2,4-Cl2-C6H3- | —O—CH2— | —CH(OH)— | m.p. 84° C. |
| 24 | 4-F3CO-C6H4- | —CH2— | —C(=O)— | $n_D^{20}$ 1.4994 |
| 25 | 4-F3CO-C6H4- | —CH2— | —CH(OH)— | $n_D^{20}$ 1.5009 |
| 26 | 2,4-Cl2-C6H3- | —CH2— | —CH(OH)— | m.p. 105° C. |
| 27 | 3,5-Cl2-C6H3- | O | —C(=O)— | m.p. 129° C. |

-continued

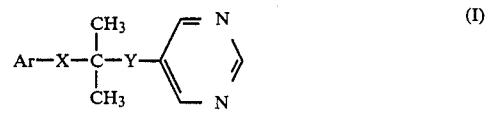

(I)

| Example No. | Ar | X | Y | Physical properties |
|---|---|---|---|---|
| 28 | 2,5-dichlorophenyl | O | —CH(OH)— | m.p. 102° C. |
| 29 | 3-chlorophenyl | —O—CH$_2$— | —CH(OH)— | m.p. 124° C. |
| 30 | 4-chlorophenyl | —S—CH$_2$— | —CH(OH)— | m.p. 141° C. |
| 31 | phenyl | —S—CH$_2$— | —C(=O)— | m.p. 89° C. |
| 32 | phenyl | —O—CH$_2$— | —C(=O)— | $n_D^{20}$ 1.5492 |
| 33 | 2-chlorophenyl | —O—CH$_2$— | —C(=O)— | $^1$H NMR:* 1.51 (6H); 4.12 (2H); 9.09 (2H); 9.29 (1H) |
| 34 | phenyl | —S—CH$_2$— | —CH(OH)— | m.p. 68° C. |
| 35 | 4-chlorophenyl | —O—CH$_2$— | —C(=O)— | m.p. 112° C. |
| 36 | 2-chlorophenyl | —O—CH$_2$— | —CH(OH)— | m.p. 90° C. |
| 37 | phenyl | —O—CH$_2$— | —CH(OH)— | m.p. 74° C. |
| 38 | 3-(trifluoromethyl)phenyl | —O—CH$_2$— | —C(=O)— | $^1$H NMR* 1.51 (6H); 4.14 (2H); 9.02 (2H); 9.30 (1H) |

-continued $$Ar-X-\underset{\underset{CH_3}{|}}{\overset{\overset{CH_3}{|}}{C}}-Y-\underset{N}{\overset{N}{\diagup}}\qquad(I)$$

| Example No. | Ar | X | Y | Physical properties |
|---|---|---|---|---|
| 39 | 4-Cl-C6H4- | —O—CH2— | —CH(OH)— | m.p. 109° C. |
| 40 | 4-Br-C6H4- | —S—CH2— | —C(=O)— | m.p. 96° C. |
| 41 | 4-Br-C6H4- | —S—CH2— | —CH(OH)— | m.p. 150° C. |
| 42 | 2-Cl-C6H4- | —S—CH2— | —C(=O)— | m.p. 59° C. |
| 43 | 2-Cl-C6H4- | —S—CH2— | —CH(OH)— | m.p. 118° C. |
| 44 | C6H5- | —S—CH2— | —C(=N—OCH3)— | $^1$H NMR*: 1.30 (6H); 3.10 (2H); 3.81 (3H) |
| 45 | 4-Br-C6H4- | —S—CH2— | —C(=N—OCH3)— | $^1$H NMR*: 1.29 (6H); 3.07 (2H); 3.80 (3H) |
| 46 | 2-Cl-C6H4- | —S—CH2— | —C(=N—OCH3)— | $^1$H NMR*: 1.29 (6H); 3.08 (2H); 3.79 (3H) |
| 47 | 4-Br-C6H4- | CH2 | —C(=O)— | m.p. 114° C. |
| 48 | C6H5- | CH2 | —C(=O)— | $^1$H—NMR*: 3.04 (2H); 1.32 (6H) |
| 49 | 4-Cl-C6H4- | S | —C(=O)— | m.p. 70° C. |

-continued

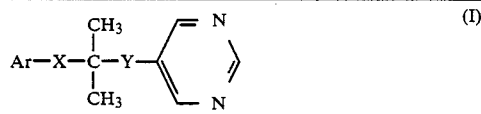

| Example No. | Ar | X | Y | Physical properties |
|---|---|---|---|---|
| 50 | Cl—⟨phenyl⟩— | S | —CH—\|OH | $^1$H—NMR*: 4.40 (1H); 8.70 (2H); 9.15 (1H) |

*The $^1$H NMR spectra were recorded in CDCl$_3$ using tetramethylsilane (TMS) as the internal standard. The chemical shift is given as the δ value in ppm.

Use examples

In the following use examples, the compounds shown below were employed as comparison substances:

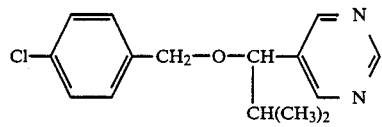

5-[1-(4-chlorobenzyloxy)-2-methyl-prop-1-yl]-pyrimidine and

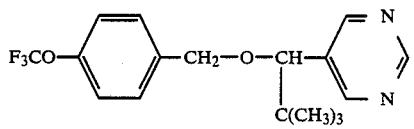

5-[1-(4-trifluoromethoxybenzyloxy)-2,2-dimethyl-prop-1-yl]-pyrimidine (both known from DE-OS (German Published Specification) 3,105,374) corresponding to U.S. Pat. No. 4436907).

Example A

Leptosphaeria nodorum test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 1, 2, 5, 8, 9, 10, 13, 14, 19, 20, 21, 24 and 25.

TABLE A

Leptosphaeria nodorum test (wheat)/protective

| Active compound | Active compound concentration in the spray Liquor in % by weight | Disease infestation in % of the untreated control |
|---|---|---|
| Cl—⟨phenyl⟩—CH$_2$—O—CH—CH(CH$_3$)$_2$ with pyrimidine (known) (A) | 0.025 | 75.0 |
| F$_3$CO—⟨phenyl⟩—CH$_2$—O—CH—C(CH$_3$)$_3$ with pyrimidine (known) (B) | 0.025 | 100 |

TABLE A-continued

| Active compound | Active compound concentration in the spray Liquor in % by weight | Disease infestation in % of the untreated control |
|---|---|---|
| (5) 4-Cl-C6H4-O-C(CH3)2-CO-O-pyrimidinyl | 0.025 | 25.0 |
| (8) 4-Cl-C6H4-S-CH2-C(CH3)2-CO-O-pyrimidinyl | 0.025 | 16.7 |
| (9) 3-Cl-C6H4-O-CH2-C(CH3)2-CO-O-pyrimidinyl | 0.025 | 33.3 |
| (10) 4-Cl-C6H4-CH2-C(CH3)2-CO-O-pyrimidinyl | 0.025 | 0.0 |
| (13) 4-CH3-C6H4-CH2-C(CH3)2-CO-O-pyrimidinyl | 0.025 | 7.5 |
| (14) 4-Cl-C6H4-CH2-C(CH3)2-CH(OH)-pyrimidinyl | 0.025 | 8.7 |
| (19) 3,4-Cl2-C6H3-CH2-C(CH3)2-CO-O-pyrimidinyl | 0.025 | 0.0 |
| (20) 3,4-Cl2-C6H3-CH2-C(CH3)2-CH(OH)-pyrimidinyl | 0.025 | 8.7 |
| (21) 2,4-Cl2-C6H3-CH2-C(CH3)2-CO-O-pyrimidinyl | 0.025 | 0.0 |
| (—) 4-F3CO-C6H4-CH2-C(CH3)2-CO-O-pyrimidinyl | 0.025 | 0.0 |

TABLE A-continued

| | Leptosphaeria nodorum test (wheat)/protective | |
|---|---|---|
| Active compound | Active compound concentration in the spray Liquor in % by weight | Disease infestation in % of the untreated control |
| (24) 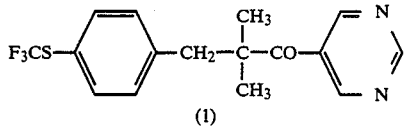 (1) | 0.025 | 3.7 |
| 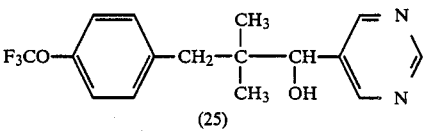 (25) | 0.025 | 0.0 |
| 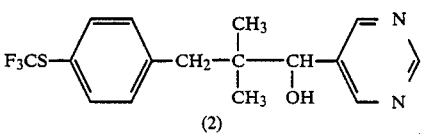 (2) | 0.025 | 0.0 |

We claim:

1. A method of combating fungi which comprises applying to such fungi or to a fungus habitat a fungicidally effective amount of a substituted pyrimidine of the formula

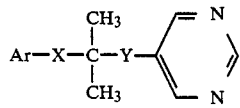

in which

Ar represents phenyl which is optionally substituted by one to three of halogen, cyano, nitro and in each case straight-chain or branched alkyl, alkoxy, alkylthio, alkylsulphinyl or alkylsulphonyl in each case having 1 to 4 carbon atoms, in each case straight-chain or branched halogenoalkyl, halogenoalkoxy, halogenoalkylthio, halogenoalkylsulphinyl or halogenoalkylsulphonyl in each case having 1 to 4 carbon atoms and 1 to 9 identical or different halogen atoms, in each case straight-chain or branched alkoxycarbonyl or alkoximinoalkyl in each case having 1 to 4 carbon atoms in the individual alkyl parts, doubly linked dioxyalkylene which is optionally monosubstituted to polysubstituted by identical or different halogen, or phenyl or phenoxy which is in each case optionally monosubstituted to polysubstituted by identical or different halogen, x represents oxygen, sulphur, sulphinyl, sulphonyl or one of the groups —CH$_2$—; —O—CH$_2$—; —CH$_2$—O—; —O—CH$_2$—CH$_2$—; —S(O)$_n$—$_{CH2}$—; —CH$_2$—S(O)$_n$—or —S(O)$_n$—CH$_2$—CH$_2$—, and Y represents one of the groups

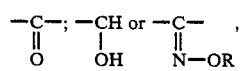

where

R represents hydrogen or in each case straight-chain or branched alkyl having 1 to 6 carbon atoms, alkenyl having 3 to 5 carbon atoms or alkinyl having 3 to 5 carbon atoms, or benzyl or phenylethyl which is in each case optionally monosubstituted to trisubstituted by identical or different substituents, suitable substituents in the phenyl part in each case being those mentioned in the case of the Ar radical, and n represents a number 0, 1 or 2, or an acid-addition salt or melt-salt complex thereof.

2. A method according to claim 1, in which

Ar represents phenyl which is optionally monosubstituted, disubstituted or trisubstituted by identical or different substituents selected from the group consisting of fluorine, chlorine, bromine, cyano, nitro, methyl, ethyl, n- or i-propyl, n-, i-, s-or t-butyl, methoxy, ethoxy, n- or i-propoxy, methylthio, ethylthio, trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethoxy, difluoromethoxy, fluoromethoxy, dichlorofluoromethoxy, difluorochloromethoxy, difluorobromomethoxy, trichloromethoxy, trifluoroethoxy, tetrafluoroethoxy, pentafluoroethoxy, trifluorochloroethoxy, trifluorodichloroethoxy, difluorotrichloroethoxy, pentachloroethoxy, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio, pentachloroethylthio, methylsulphinyl, trifluoromethylsulphinyl, dichlorofluoromethylsulphinyl, difluorochloromethylsulphinyl, fluoromethylsulphinyl, difluoromethylsulphinyl, methylsulphonyl, trifluoromethylsulphonyl, dichlorofluoromethylsulphonyl, difluorochloromethylsulphonyl, fluoromethylsulphonyl, difluoromethylsulphonyl, methoxycarbonyl, ethoxycarbonyl, methoximinomethyl, ethoximinomethyl, methoximinoethyl, ethoximinoethyl, difluorodioxymethylene, tetrafluorodioxyethylene, trifluorodioxyethylene, difluorodioxyethylene, dioxymethylene or dioxyethylene, or phenyl or phenoxy which is in each case optionally monosubstituted, disubstituted or trisubstituted by fluorine or chlorine, and R represents hydrogen, methyl, ethyl, n- or i-propyl, allyl or propargyl, or benzyl which is optionally monosubstituted, disubstituted or trisubstituted by identical or different substituents, suitable substituents being those mentioned in the case of the Ar radical.

3. The method according to claim 1, wherein such substituted pyrimidine is 1-(5-pyrimidyl)-2,2-dimethyl-3-(4-trifluoromethylthiophenyl)-propan-1-ol of the formula

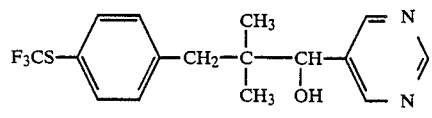

or an acid-addition salt or metal-salt complex thereof.

4. The method according to claim 1, wherein such substituted pyrimidine is 1-(5-pyrimidinyl)-2,2-dimethyl-3-(4-chlorophenyl)-propan-1-one of the formula

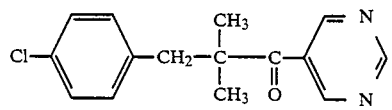

or an acid-addition salt or metal-salt complex thereof.

5. The method according to claim 1, wherein such substituted pyrimidine is 1-(5-pyrimidinyl)-2,2-dimethyl-3-(4-chlorophenyl)-propan-1-ol of the formula

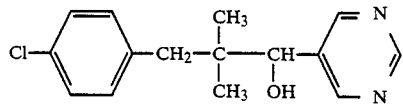

or an acid-addition salt or metal-salt complex thereof.

6. The method according to claim 1, wherein such substituted pyrimidine is 1-(5-pyrimidinyl)-2,2-dimethyl-3-(3,4-dichlorophenyl)-propan-1-one of the formula

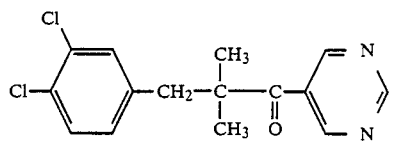

or an acid-addition salt or metal-salt complex thereof.

7. The method to claim 1, wherein such substituted pyrimidine is 1-(5-pyrimidnyl)-2,2-dimethyl-3-(2,4-dichlorophenyl)-propan-1-one of the formula

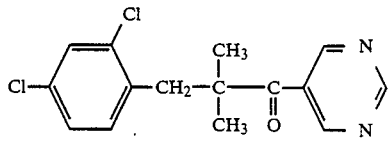

or an acid-addition salt or metal-salt complex thereof.

8. The method according to claim 1, wherein such substituted pyrimidine is 1-(5-pyrimidinyl)-2,2-dimethyl-3-(4-trifluoromethoxyphenyl)-propan-1-ol of the formula

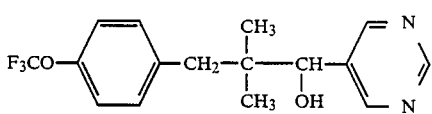

or an acid-addition salt or metal-salt complex thereof.

9. The method according to claim 1, wherein such substituted pyrimidine is 1-(5-pyrimidinyl)-2,2-dimethyl-3-(4-chlorophenoxy)-propan-1-one of the formula

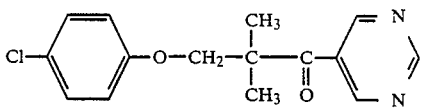

or an acid-addition salt or metal-salt complex thereof.

10. The method according to claim 1, wherein such substituted pyrimidine is 1-methoximino-1-(5-pyrimidinyl)-2,2-dimethyl-3-(4-bromophenylthio)-propane of the formula

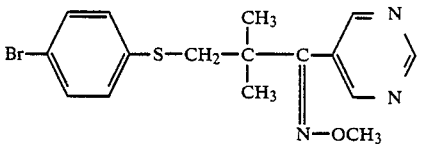

or an acid-addition salt or metal-salt complex thereof.

11. A compound selected from the group consisting of
1-(5-pyrimidyl)-2,2-dimethyl-3-(4-trifluoromethylthiophenyl)-propan-1-ol, and
1-(5-pyrimidinyl)-2,2-dimethyl-3-(4-trifluoromethoxyphenyl)-propan-1-ol,
or an acid-addition salt or metal-salt complex thereof.

12. A fungicidal composition comprising a fungicidally effective amount of a compound, salt or complex according to claim 11 and a diluent.

* * * * *